United States Patent [19]

Fletcher, Jr. et al.

[11] 4,368,247
[45] Jan. 11, 1983

[54] PHOTOGRAPHIC MATERIALS AND PROCESSES COMPRISING OXOINDOLIZINE AND OXOINDOLIZINIUM COMPOUNDS

[75] Inventors: George L. Fletcher, Jr., Pittsford, N.Y.; Steven L. Bender, Georgetown, Ill.; Donald H. Wadsworth, Rochester, N.Y.

[73] Assignee: Eastman Kodak Company, Rochester, N.Y.

[21] Appl. No.: 278,013

[22] Filed: Jun. 29, 1981

[51] Int. Cl.$^3$ .............................................. G03C 1/52
[52] U.S. Cl. ...................................... 430/17; 430/344; 430/336; 430/340; 546/121; 542/437; 542/443
[58] Field of Search ................. 430/17, 351, 338, 340, 430/334, 336; 546/121; 542/437, 443

[56] References Cited

U.S. PATENT DOCUMENTS 4,106,938  8/1978  Fletcher et al. ................. 96/48 HD
4,128,422  12/1978  Fletcher et al. ................. 96/48 HD

OTHER PUBLICATIONS

J. W. Lown et al., "Reaction of Cyclopropenones . . . ," *Canadian Jour. of Chem.*, vol. 49, (1971), pp. 1165–1175.
T. Eicher et al., "Zur Reaktion von Cyclopropenonen mit . . . ", *Tetrahedron Letters*, No. 14, (1979), pp. 1213–1216.
*Research Disclosure*, Apr., 1979, Item No. 18016.
*Research Disclosure*, Jun. 1978, Item No. 17029.
C. Holstead et al., "Some Photothermographic Systems", *The Journ. of Photo Science*, vol. 25, No. 6, Nov./Dec., 1977, pp. 241–245.

*Primary Examiner*—Won H. Louie, Jr.
*Attorney, Agent, or Firm*—Richard E. Knapp

[57] ABSTRACT

Oxoindolizine and oxoindolizinium dyes are useful in photographic materials and processes as image dyes. These dyes are formed in unexposed areas of photographic materials, especially photothermographic materials, by the reaction of a photosensitive cyclopropenone with a pyridine compound. Oxoindolizine and oxoindolizinium dyes are alternatively formed by (1) reaction of a photosensitive cyclopropenone with a pyridine compound and (2) reaction of the resulting product with a color forming coupler. The photographic material is imagewise exposed and then heated to a processing temperature to form a dye image. Alternatively, the oxoindolizine and oxoindolizinium dyes are produced by imbibing at least one of the reactants into the photographic material comprising a photosensitive cyclopropenone.

30 Claims, No Drawings

PHOTOGRAPHIC MATERIALS AND PROCESSES COMPRISING OXOINDOLIZINE AND OXOINDOLIZINIUM COMPOUNDS

BACKGROUND OF THE INVENTION

1. Field of the Invention

This invention relates to photographic materials comprising oxoindolizine and oxoindolizinium dye images. It also relates to the formation of such dye images in photographic materials.

2. Description of the State of the Art

Formation of image dyes in photographic materials is well known in the photographic art. However, a continuing need has existed for new classes of image dyes which are capable of a range of absorption and are formed in a photographic material without the need for complex multistep reactions.

Preparation of images without the need for silver, such as without the need for photographic silver halide, is known in the photographic art. The use of photosensitive cyclopropenones for forming vesicular images has been described as one form of such imaging. This is described in, for example U.S. Pat. Nos. 4,106,938 and 4,128,422. It has been desirable to provide a photographic material that enables formation of new image dyes that have a wide range of absorption by means of photosensitive cyclopropenones.

SUMMARY OF THE INVENTION

According to the invention, an oxoindolizine or oxoindolizinium dye is formed in a photographic material, such as a photothermographic material. Such a dye is provided by reacting a photosensitive cyclopropenone and a pyridine compound. The photographic material alternatively also comprises a color-forming compound, such as a phenolic, aniline, or active methylene color-forming coupler, which enables formation of a second oxoindolizine or oxoindolizinium dye.

The photosensitive cyclopropenone forms a compound in the exposed areas of the photographic material which compound does not react with the pyridine compound such as upon heating. The compound formed from the exposed photosensitive cyclopropenone does not react with a color-forming coupler. The photosensitive cyclopropenone and the pyridine compound in unexposed areas react to form an oxoindolizine or oxoindolizinium compound. This oxoindolizine or oxoindolizinium compound is in some cases a dye. In other cases the resulting compound dimerizes to form the desired dye.

In the case of a photographic material comprising a color-forming coupler, the initial oxoindolizine or oxoindolizinium compound formed further reacts with the color-forming coupler to form a second oxoindolizine or oxoindolizinium compound which absorbs at a different wavelength from the initial oxoindolizine or oxoindolizinium compound formed. The oxoindolizine or oxoindolizinium compounds formed in both cases are dyes in the unexposed areas forming a positive image.

The oxoindolizine and oxoindolizinium compounds formed in exposed and processed photographic materials according to the invention are novel image compounds. These novel image compounds do not require photographic silver halide or other silver compounds for image formation. These compounds also absorb at various wavelengths of the electromagnetic spectrum.

DETAILED DESCRIPTION OF THE INVENTION

Particularly useful oxoindolizine and oxoindolizinium dyes formed in a photographic element according to the invention are selected from the group consisting of methyleneoxoindolizine, (4-oxoarylene)oxoindolizine, bis-oxoindolizine, bis(oxoindolizinyl) ethylene, (2- and 4-amino-arylene)oxoindolizine and pyridiniumoxoindolizine dyes. Oxoindolizine and oxoindolizinium dyes according to the invention are in their keto or enol form. The invention also includes these dyes in their various isomeric and tautomeric forms.

Oxoindolizine dyes formed in a photographic element according to the invention in their keto form have the following structure:

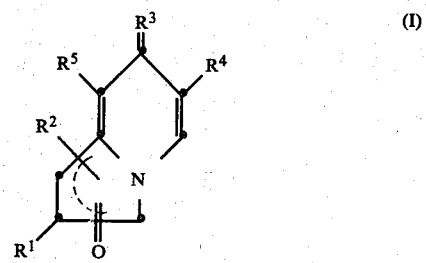

wherein $R^1$ and $R^2$ are individually selected from straight and branched alkyl containing 1 to 18, preferably 1 to 10 carbon atoms, such as methyl, ethyl, propyl and decyl;

aryl containing 6 to 20 carbon atoms, such as phenyl, tolyl, xylyl, methoxyphenyl, 4-t-butylphenyl, anisyl, naphthyl and methoxynaphthyl; and polystyryl having appended groups selected from the group consisting of indolizine and indolizinium groups and combinations thereof;

$R^3$ is a divalent group which with the oxoindolizine nucleus completes an organic chromophore;

$R^4$ is hydrogen or a substituent that does not adversely affect desired dye properties, such as alkyl containing 1 to 18 carbon atoms, such as methyl, ethyl and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine; and $R^5$ is hydrogen or a substituent that does not adversely affect desired dye properties, such as hydrogen, chlorine, bromine or alkyl containing 1 to 18 carbon atoms, such as methyl, ethyl, propyl, and dodecyl.

Oxoindolizinium dyes formed in a photographic element according to the invention in their keto form are within the following structure:

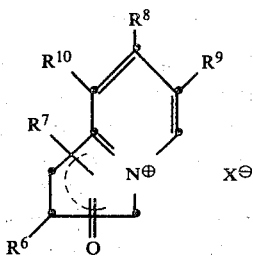

(II)

wherein $X^\ominus$ is an anion, such as methanesulfonate, trifluoromethanesulfonate, para-toluenesulfonate, bromide, chloride, iodide, and sulfinate, preferably an acid anion;

$R^6$ and $R^7$ are individually alkyl containing 1 to 18, preferably 1 to 10 carbon atoms, such as methyl, ethyl, propyl and decyl;

aryl containing 6 to 20 carbon atoms, such as phenyl, tolyl, xylyl, methoxyphenyl, 4-t-butylphenyl, anisyl, naphthyl and methoxynaphthyl; and polystyryl having appended groups selected from the group consisting of indolizine and indolizinium groups and combinations thereof;

$R^8$ is a monovalent group which with the oxoindolizinium nucleus completes an organic chromophore;

$R^9$ is hydrogen or a substituent that does not adversely affect desired dye properties, such as alkyl containing 1 to B 18 carbon atoms, such as methyl, ethyl, and dodecyl; cyano; acyl containing 2 to 18 carbon atoms, such as acetyl, propionyl, 2-ethylhexanoyl and stearolyl; carboalkoxy containing 1 to 18 carbon atoms, such as carbomethoxy, carboethoxy and carbobutoxy; aminocarbonyl, such as unsubstituted aminocarbonyl, methylcarbonyl, dimethylaminocarbonyl, and ethylaminocarbonyl; acyloxy containing 2 to 18 carbon atoms, such as acetoxy, propionoxy, butyroxy and lauroyloxy; bromine and chlorine; and $R^{10}$ is hydrogen or a substituent that does not adversely affect desired dye properties, such as hydrogen, chlorine, bromine or alkyl containing 1 to 18 carbon atoms, such as methyl, ethyl, propyl and dodecyl.

Useful $R^3$ and $R^8$ groups are, for example (a) substituted or unsubstituted heterocyclyl or heterocyclylidene groups optionally appended through methine and polymethine groups, such as (i) indolizine and indolizinium groups illustrated by structures (I) and (II) appended directly as the respective $R^3$ and $R^8$ groups or appended through a substituted or unsubstituted methine or polymethine chain, such as containing 1 to 6 methine groups, (ii) pyridylidene, (iii) pyranyl, (iv) pyranylidene, (v) thiopyranyl, (vi) thiopyranylidene, and (vii) julolidyl; including the onium salts of such heterocyclyl and heterocyclylidene groups, such as the immonium, oxonium and sulfonium salts; and the acid addition salt derivatives of such heterocyclyl and heterocyclylidene groups;

(b) substituted and unsubstituted aminoarylmethine and hydroxyarylmethine, including their tautomers, such as represented by the formula: (Z) (A) (D) wherein Z is a methine or polymethine group, such as containing 1 to 6 methine groups;

A is a substituted or unsubstituted aromatic group, such as arylene containing 6 to 20 carbon atoms, for example, phenylene, phenylidene, naphthylene, and naphthylidene; and D is $—OR^{11}$, $—NR^{12}R^{13}$, $=O$, or $=NR^{14}$ wherein $R^{11}$ is a monovalent cation, preferably hydrogen, $R^{12}$ and $R^{13}$ are independently elected from hydrogen, substituted or unsubstituted alkyl, such as alkyl containing 1 to 20 carbon atoms, alkenyl, such as alkenyl containing 2 to 20 carbon atoms, and aryl, such as aryl containing 6 to 20 carbon atoms, including phenyl and tolyl; or, $R^{12}$ and $R^{13}$ taken together with (A) form a polycyclic heterocyclic group, such as a 9-julolidyl group;

$R^{14}$ is alkyl, such as alkyl containing 1 to 20 carbon atoms or aryl, such as aryl containing 1 to 20 carbon atoms;

(c) a methylene group substituted with at least one, preferably two electronegative groups, such as acyl, cyano, aryl, alkoxycarbonyl, and aminocarbonyl groups; and (d) a formyl group.

$X^\ominus$ is an anion as defined above, for example, methanesulfonate, trifluoromethanesulfonate, para-toluenesulfonate, bromide, chloride, iodide, and sulfinate.

The term "enol" herein means an enol from the keto form of the dye as well as an enol produced by a protonation reaction or other reaction. For example, typical enols are represented by the formula:

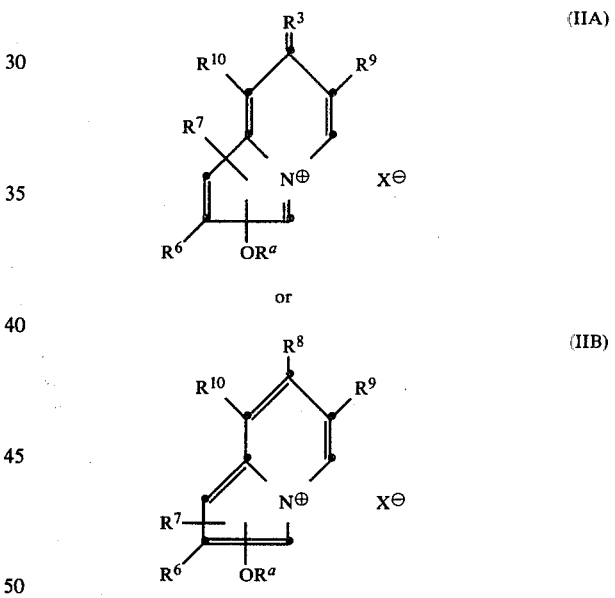

wherein $X^\ominus$, $R^3$, $R^6$, $R^7$, $R^8$, $R^9$ and $R^{10}$ are as defined and $R^a$ is hydrogen or acyl.

The term "acyl" herein means alkylcarbonyl containing 2 to 20 carbon atoms and arylcarbonyl, such as arylcarbonyl containing 7 to 20 carbon atoms.

The term "aryl" herein means unsubstituted aryl and substituted aryl. Aryl herein includes, for example, aryl containing 6 to 20 carbon atoms, such as phenyl, tolyl, xylyl, naphthyl, and methoxyphenyl.

The formation of oxoindolizine and oxoindolizinium dyes according to the invention does not involve complicated reaction steps as do the preparations of other dyes.

The oxoindolizine and oxoindolizinium dyes according to the invention are prepared by (1) reaction of a cyclopropenone compound with a pyridine compound, or (2) reaction of a cyclopropenone compound with a pyridine compound and then with a color-forming coupler.

The pyridine compound herein does not include a pyridine which contains a substituent in the 2-position or 6-position on the pyridine ring. It was found that in reactions (1), (2) and (3) that the pyridine compound does not form an indolizinone or indolizinium dye when the pyridine compound contains a substituent in the 2-position or 6-position on the pyridine ring, that is in the position on the ring next to the ring nitrogen atom.

The dyes formed are identified by analytical methods known in the chemical arts, such as nuclear magnetic resonance (NMR) analysis, infrared analysis, elemental analysis, melting point, or combinations of these, as well as the color of the dye.

Many pyridine compounds are useful in forming a dye according to the invention. Examples of useful pyridine compounds are represented by the formula:

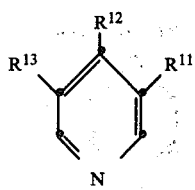
(III)

wherein:

$R^{11}$ is hydrogen, alkyl containing 1 to 18 carbon atoms, such as methyl, ethyl and dodecyl; cyano, acyl containing 2 to 18 carbon atoms, such as acetyl, propionyl, 2-ethylhexanoyl and stearoyl; carboalkoxy, containing 1 to 18 carbon atoms, such as carbomethoxy, carboethoxy and carbobutoxy; aminocarbonyl, such as unsubstituted aminocarbonyl, methylaminocarbonyl, acyloxy containing 2 to 18 carbon atoms, such as acetoxy, propionoxy, butyroxy and lauroyloxy; bromine and chlorine;

$R^{12}$ is hydrogen, alkyl containing 1 to 18 carbon atoms, such as methyl, ethyl, propyl and dodecyl; cyano; acyl containing 2 to 18 carbon atoms, such as acetyl propionyl, butyryl and lauryl; benzyl or pyridyl; and $R^{13}$ is hydrogen, chlorine, bromine or alkyl containing 1 to 18 carbon atoms, such as methyl, ethyl, propyl and dodecyl.

Combinations of pyridine compounds are also useful.

Examples of useful pyridine compounds for preparation of dyes according to the invention are:

P-1    4,4'-Dipyridylethylene:

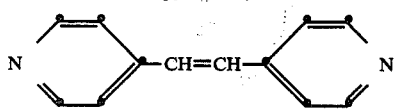

P-2    1-Methyl-4-(4-pyridyl)pyridinium-p-toluene-sulfonate:

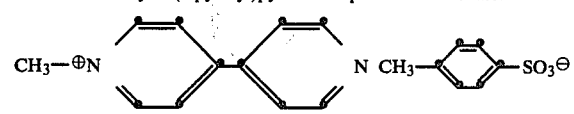

P-3    Pyridine:

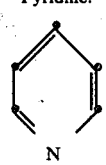

P-4    4-Picoline:

P-5    4-Formylpyridine (also known as 4-pyridinecarboxaldehyde):

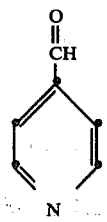

P-6    4-(4-Azastyryl)-1-methylpyridinium p-toluene-sulfonate:

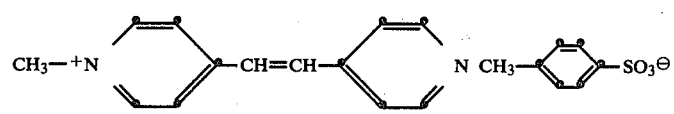

P-7    4-Acetylpyridine:

P-8    3-Acetylpyridine:

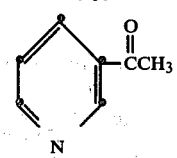

P-9    3-Benzylpyridine:

P-10    4-Benzylpyridine:

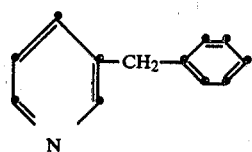
| | | | |
|---|---|---|---|
| P-11 | 3-Bromopyridine: 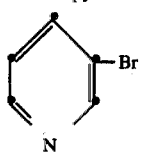 | P-12 | 4-(p-chlorobenzyl)pyridine: 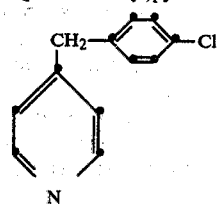 |
| P-13 | 3-Chloropyridine: 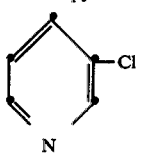 | P-14 | 3-Cyanopyridine: 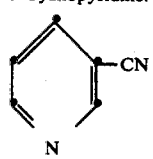 |
| P-15 | 3,5-Dichloropyridine: 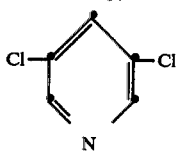 | P-16 | N,N—diethylnicotinamide: 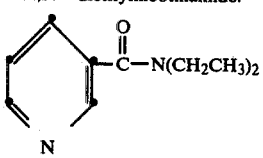 |
| P-17 | 3-Ethylpyridine: 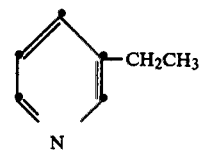 | P-18 | 4-Ethylpyridine: 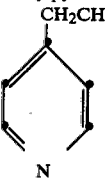 |
| P-19 | Ethyl 3-pyridylacetate: 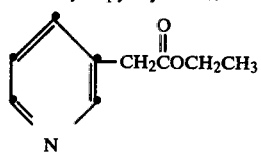 | P-20 | 3,4-Lutidine: 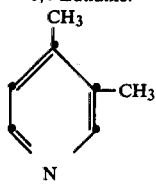 |
| P-21 | 3,5-Lutidine: 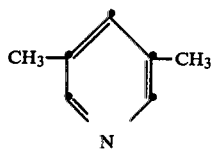 | P-22 | 2-Methyl-1,2-di-3-pyridyl-1-oxo-propane: 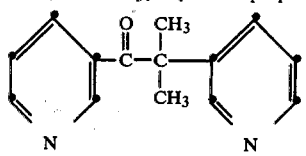 |
| P-23 | N—methylnicotinamide: 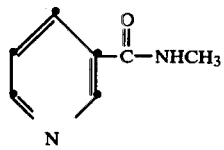 | P-24 | Methyl nicotinate: 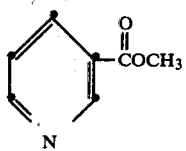 |
| P-25 | 3-Picoline: | P-26 | 3-Formylpyridine (also known as 3-Pyridinecarboxaldehyde): |

P-27  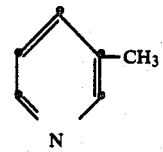
3-Cyanomethylpyridine (also known as 3-Pyridylacetonitrile):

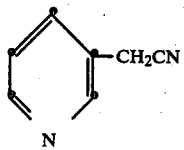

P-20  Trans-1-(3-pyridyl)-2-(4-pyridyl)ethylene:

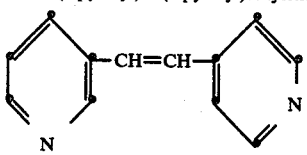

P-31  1-Benzyl-4-(4-pyridyl)pyridinium bromide:

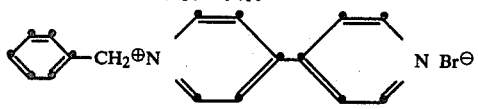

P-28  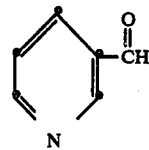
3-(3-pyridyl)-1-propanol:

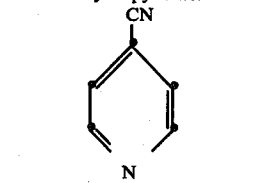

P-30  4-Cyanopyridine:
CN

P-32  4-(4-Nitrophenyl)pyridine:

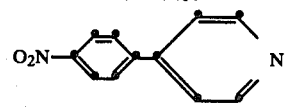

Many cyclopropenones are useful for forming dyes according to the invention. Examples of useful cyclopropenones are cyclopropenones represented by the formula:

$$R^{14}-C{\overset{\overset{\displaystyle O}{\|}}{\overset{\displaystyle C}{\diagup\!\diagdown}}}C-R^{15} \qquad (IV)$$

wherein:

R$^{14}$ and R$^{15}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl(2-phenylvinyl); alkyl containing 1 to 20, preferably 1 to 10 carbon atoms, such as methyl, ethyl, propyl, decyl and eicosyl; or R$^{14}$ and R$^{15}$ together represent the carbon atoms necessary to complete a cyclic structure, for example, a 7- or 8-member cyclic structure, such as 2,3-pentamethylene. The aryl group of R$^{14}$ and R$^{15}$ is unsubstituted or substituted by one or more groups selected from the group consisting of:

(1) alkyl or alkoxy containing 1 to 5 carbon atoms, for example, methyl, ethyl, propyl, isopropyl, butyl, methoxy, ethoxy, propoxy and butoxy;

(2) nitro;

(3) aryloxy containing 6 to 10 carbon atoms, such as phenoxy and naphthoxy;

(4) halogen, for example, chlorine, fluorine, iodine and bromine;

(5) a homopolymer or copolymer to which the aryl group is attached as a pendant moiety with the polymer having at least one repeating unit represented by the formula:

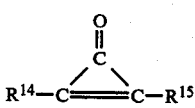

wherein:

R$^{16}$ is a lower alkylene group containing from 1 to 5 carbon atoms, such as ethylene and propylene; and z is at least a portion of the number of repeating units in a polymer chain. The number of cyclopropenone units must be sufficient to provide a desired image. Combinations of cyclopropenones are also useful according to the invention.

Examples of useful cyclopropenones are described in U.S. Pat. No. 4,128,422. Useful cyclopropenones are photosensitive cyclopropenones. Particularly useful cyclopropenones that are useful in forming oxoindolizine and oxoindolizinium compounds according to the invention are not particularly sensitive to wavelengths of radiation in the visible region of the spectrum. Radiation in other regions of the electromagnetic spectrum is useful for such compounds.

Examples of useful cyclopropenones are:
2,3-diphenylcyclopropenone
2-(2-methoxynaphthyl)-3-phenylcyclopropenone
2-(2-methoxynaphthyl)-3-(4-methoxyphenyl)cyclopropenone
2,3-bis(2-methoxynaphthyl)cyclopropenone
2,3-bis(2,4-dimethylphenyl)cyclopropenone
2,3-bis(4-n-butoxyphenyl)cyclopropenone
2,3-bis(4-methoxyphenyl)cyclopropenone poly[styrene-co-4-(2-phenylcyclopropenoyl)styrene]
2,3-bis(4-phenoxyphenyl)cyclopropenone
2-(4-n-butoxyphenyl)-3-phenylcyclopropenone
2-(2,5-dimethylphenyl)-3-phenylcyclopropenone
2-(4-methoxyphenyl)-3-phenylcyclopropenone
2-(2,4-dimethoxyphenyl)-3-phenylcyclopropenone 2,3-bis(2,4-dimethoxyphenyl)cyclopropenone
2,3-bis(2-methyl-5-isopropylphenyl)cyclopropenone
2,3-bis(3-nitrophenyl)cyclopropenone
2,3-bis(2,5-dimethylphenyl)cyclopropenone
2,3-bis(4-methylphenyl)cyclopropenone
2,3-di-n-propylcyclopropenone
2,3-pentamethylenecyclopropenone
2-(2,4-dimethoxyphenyl)-3-(2,4-dimethylphenyl)-cyclopropenone
2,3-bis(2,5-dimethoxyphenyl)cyclopropenone
2-(2,4,6-trimethylphenyl)-3-phenylcyclopropenone
2-phenyl-3-(2,5-dimethoxyphenyl)cyclopropenone
2-phenyl-3-(2,4-dimethylphenyl)cyclopropenone
2,3-bis(2,2-diphenylvinyl)cyclopropenone
2,3-bis(2-methyl-2-phenylvinyl)cyclopropenone The described cyclopropenones are prepared by processes known in the organic synthesis art.

The cyclopropenones are spectrally sensitized, if desired. Spectral sensitization procedures and compounds for spectrally sensitizing cyclopropenones are known in the photographic art, such as described in U.S. Pat. No. 4,128,422. Useful spectral sensitizers are, for example: 2-benzoylmethylene-3-methylnaphthyl-(2,1-d)thiazoline; 3-carboxymethyl-5-(3-ethylbenzothiazolinylidine)rhodanine; anhydro-3,3'-disulfopropyl-5-methoxythiacyaninehydroxide; 2-[bis(2-furoyl)-methylene]-1-methylnaphthyl-[1,2-d]-thiazoline; and 3-benzoyl-7-methoxycoumarin. Combinations of spectral sensitizers are also useful.

Especially useful phenolic couplers, aniline couplers and active methylene couplers for forming dyes according to the invention are couplers which are useful in the photographic art for producing dye images.

The term "phenolic coupler" herein means a phenolic compound or naphtholic compound which forms a dye by reaction with an oxoindolizine or oxoindolizinium compound according to the invention.

Examples of useful phenolic couplers are represented by the formula:

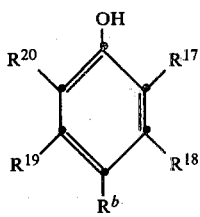

(VI)

wherein:

$R^b$, $R^{17}$, $R^{18}$, $R^{19}$ and $R^{20}$ individually represent substituents which do not adversely affect the desired oxoindolizine and oxoindolizinium dyes, such as by altering the solubility or desired hue, and individually represent substituents that are useful in phenolic couplers in the photographic art, such as described in, for example, U.S. Pat. No. 3,620,747, the description of which is incorporated herein by reference. In Structure VI at least one of $R^{17}$, $R^{20}$ and $R^b$ is hydrogen. For example, $R^b$, $R^{17}$ and $R^{18}$ are individually hydrogen; hydroxyl; alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen; such as chlorine, fluorine, bromine and iodine; and alkoxy containing 1 to 18 carbon atoms, such as methoxy, ethoxy and propoxy;

$R^{19}$ and $R^{20}$ are individually hydrogen, alkyl containing 1 to 22 carbon atoms, such as methyl, ethyl, propyl and decyl; aryl containing 6 to 20 carbon atoms, such as phenyl and tolyl; amino; carboxamido; sulfonamido, sulfamyl; carbamyl; halogen, such as chlorine, fluorine, bromine and iodine; and alkoxy containing 1 to 18 carbon atoms, such as methoxy, ethoxy and propoxy; or $R^{19}$ and $R^{20}$ taken together represent the atoms necessary to complete a benzo group which is unsubstituted or substituted by at least one of the groups given for $R^{17}$. Combinations of phenolic couplers are also useful.

Examples of useful phenolic couplers are:

C-1  2-Acetylamino-5-methylphenol

C-2  2-[α-(4'-tert.-amylphenoxy)-butyrylamino]-5-methyl-1-phenol

C-3  2-cyanoacetamidophenol

C-4  2-(2-stearoyloxyethyl)iminomethylphenol

C-5  2-octadecyloxyphenol

C-6  2-perfluorobutyramido-5-propionamidophenol

C-7  2-octadecyl aminocarbonyl-1-naphthol

C-8  2-(2-sulfonoxy-4-stearoylamino-anilinocarbonyl)-1-naphthol

C-9  2-(propylaminocarbonyl)-1-naphthol

C-10  2-[α-(4-tert-amylphenoxy)butyryl-aminophenol]
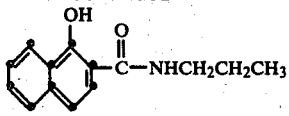

C-11  2-(N—methylanilinocarbonyl)-1-naphthol
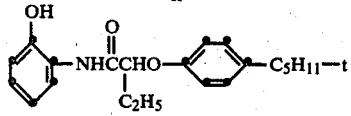

C-12  2-[2-(2-acetamidophenyl)ethyl-aminocarbonyl]-1-naphthol
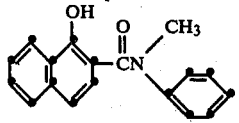

C-13  2-(4-tert-butylbenzamido-resorcinol)
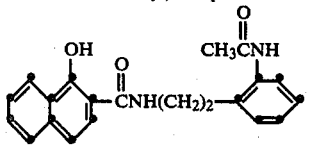

C-14  resorcinol
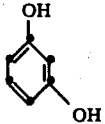

C-15  2-(2-amyloxybenzamido)resorcinol
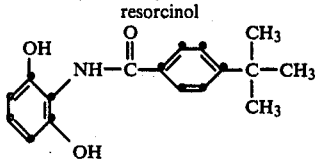

C-16  bis-4,4'-resorcinyl sulfide
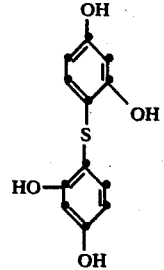

C-17  2-propinoamidoresorcinol
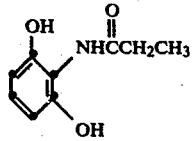

C-18  2-benzamidoresorcinol
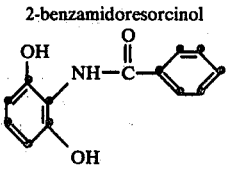

C-19  2,6-di-tert-butylphenol
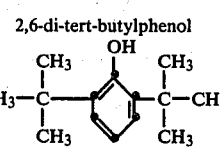

The term "aniline coupler" herein means an aniline compound or related derivative which forms a dye by reaction with an oxoindolizine or oxoindolizinium compound according to the invention.

Examples of useful aniline couplers and derivatives thereof useful in forming oxoindolizine and oxoindolizinium dyes according to the invention are represented by the formulas:

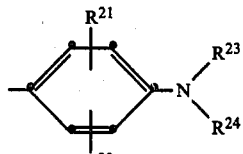
(VI)

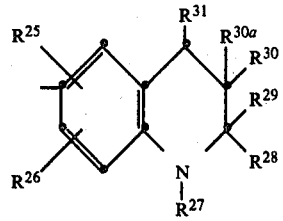
(VII)

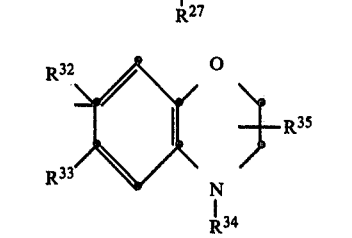
(VIII)

wherein $R^{21}$, $R^{22}$, $R^{25}$, $R^{26}$, $R^{32}$ and $R^{33}$ are individually hydrogen; fluorine; chlorine; bromine; alkyl containing 1 to 6 carbon atoms; cycloalkyl containing 3 to 10 carbon atoms; alkoxy containing 1 to 4 carbon atoms; phenoxy; alkylthio, such as alkylthio containing 1 to 4 carbon atoms; arylthio, such as arylthio containing 6 to 20 carbon atoms; and groups represented by the formula —NH—X—$R^{36}$ in which X is —CO—, —COO— or —SO$_2$—;

$R^{23}$, $R^{24}$, $R^{27}$ and $R^{34}$ are individually selected from hydrogen; cycloalkyl, such as cycloalkyl containing 6 to 20 carbon atoms; straight or branched alkenyl containing 2 to 10 carbon atoms; alkyl containing 1 to 18 carbon atoms, or $R^{23}$ and $R^{24}$ together represent the atoms necessary to complete a 5- or 6-member heterocyclic ring with the nitrogen atom to which they are bonded, such as atoms completing a pentamethylene, ethyleneoxyethylene or ethylenesulfonylethylene group which forms a ring or a julolidyl group;

$R^{28}$, $R^{29}$, $R^{30}$, $R^{30a}$, $R^{31}$ and $R^{35}$ are individually selected from hydrogen and alkyl containing 1 to 6 carbon atoms;

$R^{36}$ is alkyl containing 1 to 6 carbon atoms or alkyl substituted by a group that does not adversely affect the desired indolizinone or indolizinium dye, such as halogen, hydroxy, phenoxy, aryl, such as aryl containing 6 to 20 carbon atoms, cyano, cycloalkyl, such as cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms and alkoxy containing 1 to 6 carbon atoms; when X is —CO—, then $R^{36}$ is also selected from hydrogen, amino, alkenyl containing 2 to 6 carbon atoms, alkylamino containing 1 to 6 carbon atoms, alkylcarbamoyl containing 1 to 6 carbon atoms, dialkylamino containing 2 to 12 carbon atoms, arylamino containing 6 to 12 carbon atoms, aryl containing 6 to 20 carbon atoms and furyl.

When $R^{23}$, $R^{24}$, $R^{27}$, or $R^{34}$ are alkyl, the alkyl is unsubstituted or substituted by, for example, hydroxy, halogen, cyano, alkoxy containing 1 to 6 carbon atoms, alkoxyalkoxy containing 2 to 8 carbon atoms, hydroxyalkoxy containing 1 to 4 carbon atoms, succinimido, glutarimido, phenylcarbamoyloxy, phthalimido, phthalimidino, 2-pyrrolidono, cyclohexyl, phenoxy, phenyl or phenyl substituted by alkyl containing 1 to 6 carbon atoms, alkoxy containing 1 to 6 carbon atoms, halogen, alkanoylamino containing 1 to 6 carbon atoms; cyano or alkoxycarbonyl containing 2 to 6 carbon atoms; sulfamoyl; alkylsulfamoyl containing 1 to 6 carbon atoms; vinylsulfonyl; acrylamido; phthalimido; alkylsulfonamido, such as alkylsulfonamido containing 1 to 6 carbon atoms; phenylsulfonamido; alkoxycarbonylamino containing 1 to 6 carbon atoms; alkylcarbamoyloxy containing 1 to 6 carbon atoms; alkoxycarbonyloxy containing 1 to 6 carbon atoms; alkenylcarbonylamino containing 3 to 6 carbon atoms; groups represented by the formula:

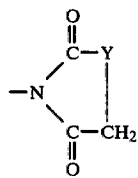

wherein
Y is —NH—,

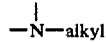

containing 1 to 6 carbon atoms, —O—, —S—, or —CH$_2$O—; —S—$R^{37}$ wherein $R^{36}$ is alkyl containing 1 to 6 carbon atoms, phenyl, phenyl substituted with halogen, alkoxy containing 1 to 6 carbon atoms, alkanoylamino containing 1 to 6 carbon atoms, cyano or lower alkoxycarbonyl, pyridyl, pyrimidinyl, benzoxazolyl, benzimidazolyl, benzothiazolyl, triazolyl; SO$_2$R$^{39}$; —COOR$^{40}$; —OXR$^{41}$; —NH—X—R$^{42}$; —X—R$^{43}$; —OCO—R$^{44}$; —CONR$^{45}$R$^{46}$; —SO$_2$NHR$^{47}$; —SO$_2$NR$^{48}$R$^{49}$; wherein $R^{39}$, $R^{40}$, $R^{41}$, $R^{42}$, $R^{43}$ and $R^{44}$ are individually selected from unsubstituted alkyl containing 1 to 6 carbon atoms and alkyl containing 1 to 6 carbon atoms substituted by at least one group that does not adversely affect the desired indolizinone or indolizinium dye, such as halogen, hydroxy, phenoxy, aryl containing 6 to 20 carbon atoms, cyano, cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms; and alkoxy containing 1 to 6 carbon atoms, and when X is —CO—, then $R^{41}$, $R^{42}$ and $R^{43}$ are also individually selected from hydrogen, amino, alkenyl containing 2 to 6 carbon atoms, alkylamino containing 1 to 6 carbon atoms, alkyl carbamoyl containing 2 to 6 carbon atoms, dialkylamino containing 2 to 6 carbon atoms, arylamino containing 6 to 20 carbon atoms, aryl containing 6 to 20 carbon atoms or furyl;

$R^{45}$, $R^{46}$, $R^{47}$, $R^{48}$ and $R^{49}$ are individually selected from hydrogen, unsubstituted alkyl containing 1 to 6 carbon atoms and alkyl containing 1 to 6 carbon atoms substituted by at least one group that does not adversely affect the desired oxoindolizine or oxoindolizinium dye, such as halogen, hydroxy, phenoxy, aryl containing 6 to 20 carbon atoms, cyano, cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms and alkoxy containing 1 to 6 carbon atoms, cyano, alkanoyloxy containing 1 to 6 carbon atoms, phenoxy, phenoxy substituted by at least one of alkyl containing 1 to 6 carbon atoms, alkoxy containing 1 to 6 carbon atoms, and halogen.

The term "cycloalkyl" herein means an unsubstituted cycloalkyl group or a cycloalkyl group containing substituents that do not adversely affect an oxoindolizine or oxoindolizinium dye according to the invention. The cycloalkyl group, for example, contains 3 to 7 carbon atoms and is unsubstituted or substituted by one or two groups selected from alkyl containing 1 to 4 carbon atoms, hydroxyl, alkoxy containing 1 to 4 carbon atoms, phenyl or phenyl containing an alkyl group containing 1 to 4 carbon atoms, alkoxy containing 1 to 4 carbon atoms, halogen, alkanoylamino, cyano and alkoxycarbonyl, such as alkoxycarbonyl containing 1 to 4 carbon atoms. Combinations of aniline couplers are also useful.

Examples of useful aniline couplers are as follows:

AN-1  N,N—dimethylaniline

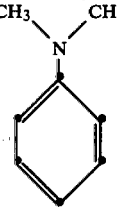

AN-2  julolidine

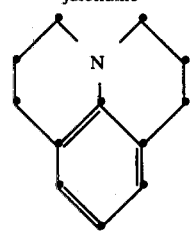

AN-3  N,N—diethylaniline

CH₃CH₂—N—CH₂CH₃

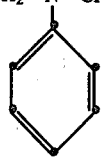

AN-4  N—phenylpiperidine

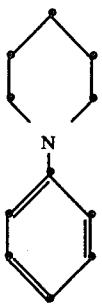

Examples of useful active methylene couplers for forming dyes according to the invention are represented by the formula:

$$Y^1 - \overset{H}{\underset{Y^3}{C}} - Y^2 \qquad (IX)$$

wherein:

Y¹ and Y² are the same or different electronegative groups, such as aryl containing 6 to 20 carbon atoms, such as phenyl and naphthyl; cyano; acyl containing 2 to 18 carbon atoms, such as acetyl, propionyl and butyryl; carboalkoxy containing 1 to 18 carbon atoms, such as carbomethoxy, carboethoxy, carbobutoxy and carboamyloxy; aminocarbonyl containing 1 to 18 carbon atoms, such as unsubstituted aminocarbonyl, methylaminocarbonyl, dimethylaminocarbonyl and ethylaminocarbonyl; or oxo-, thio- or selenopyrylium; or oxoindolizinium; or Y² is hydrogen; and Y³ is hydrogen or halogen, such as chlorine, bromine and iodine. Preferred active methylene couplers are ketomethylene couplers. Other useful active methylene couplers include those known to be useful in the photograpic art, such as pyrazalinone and coumarin couplers. Combinations of active methylene couplers are also useful.

Examples of preferred ketomethylene couplers are represented by the formula:

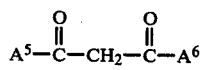

wherein:

A⁵ and A⁶ are individually selected from alkyl containing 1 to 18 carbon atoms, such as methyl, ethyl, propyl and amyl; aryl containing 6 to 14 carbon atoms, such as phenyl, naphthyl and anthryl; hydroxy; alkoxy, such as alkoxy containing 1 to 6 carbon atoms; amino; substituted amino; or thiol.

Ketocarboxamides are examples of especially useful ketomethylene couplers for forming dyes according to the invention. Examples of useful ketocarboxamides are represented by the formula:

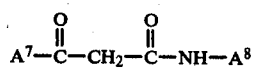

wherein:

A⁷ and A⁸ are individually selected from alkyl containing 1 to 18 carbon atoms, such as methyl, ethyl, propyl, butyl, amyl, decyl and stearyl; and aryl containing 6 to 14 carbon atoms, such as phenyl, naphthyl, and anthryl; carbonyl; amino and vinyl.

Other particularly useful active methylene couplers are alkyl flavylium salts and alkyl pyrylium salts, such as described in U.S. Pat. Nos. 3,141,770 and 3,250,615.

Examples of useful methylene couplers include the following:

M-1  2,6-Diphenyl-4-methylpyrylium perchlorate

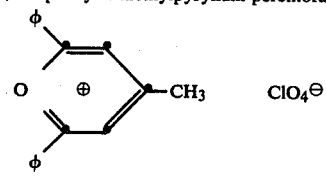

M-2  2,4-Diphenyl-6-methylpyrylium perchlorate

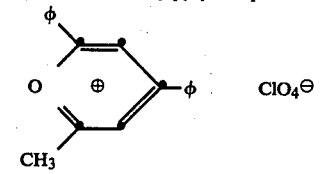

M-3  2,6-Diphenyl-4-methylthiopyrylium perchlorate

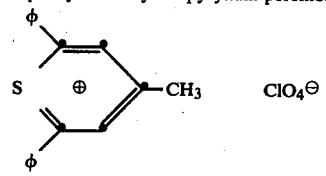

M-4  4-Methyl-2-phenylflavylium perchlorate

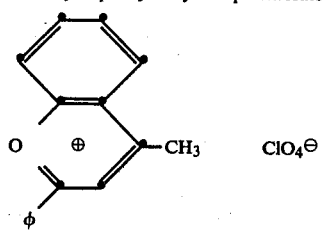

M-5  2-Methyl-4-phenylflavylium perchlorate

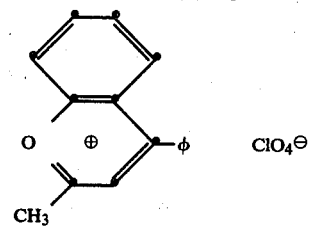

M-6  4-Methyl-2-phenylthioflavylium perchlorate

-continued

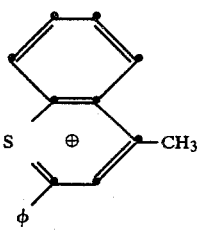  ClO₄⁻

M-7  2,6-di-(2-thiopheneyl)-4-methylpyrylium fluoborate

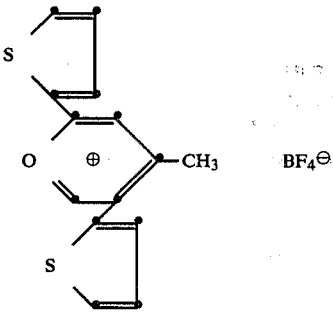  BF₄⁻

M-8  2-(4-methoxyphenyl)-4-methylthioflavylium perchlorate

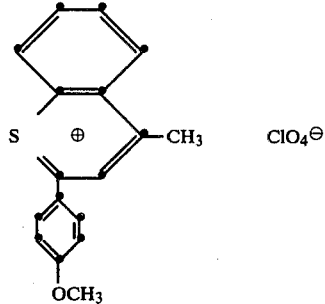  ClO₄⁻

M-9  2,4-pentanedione
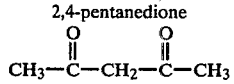

M-10  dibenzoylmethane
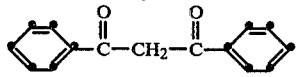

M-11  1-anilino-3-phenyl-1,3-propanedione
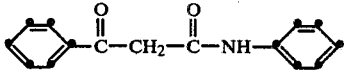

M-12
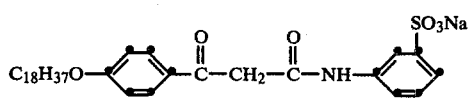

M-13  1-tert-butyl-3-(4-methoxy anilino)-1,3-propane dione
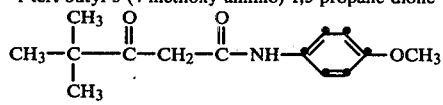

M-14  malononitrile
CH₂(CN)₂

M-15  phenylacetonitrile
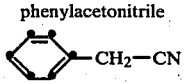

M-16  phenylacetamide
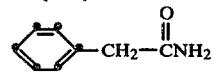

M-17  N—phenyl acetylacetamide
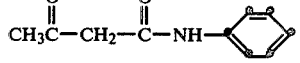

M-18  bis-nitrophenylmethane
CH₂(C₆H₄NO₂)₂

M-19  methyl cyanoacetate
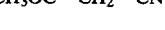

M-20  2,2-dimethyl-m-dioxane-4,6-dione
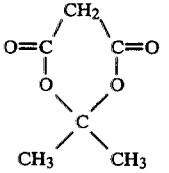

M-21  cyanoacetamide
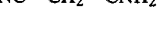

The designation φ herein means a phenyl group.

Other particularly useful active methylene couplers are salts represented by the formula:

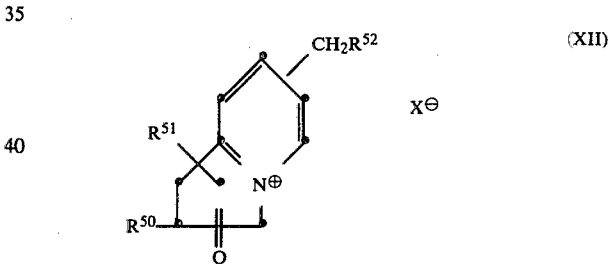

wherein $R^{50}$ and $R^{51}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl(2-phenylvinyl); alkyl containing 1 to 20 carbon atoms, such as methyl, ethyl, propyl, decyl and eicosyl; or $R^{50}$ and $R^{51}$ together represent the carbon atoms necessary to complete a cyclic structure, such as 2,3-pentamethylene; and $R^{52}$ is a substituent which does not interfere with coupling action of the indolizinium salt and does not adversely affect the desired properties of a resulting indolizinium or indolizinone dye, such as hydrogen; carboxyl; alkyl containing 1 to 18 carbon atoms, for example, methyl, ethyl, propyl and dodecyl; cyano; and, aryl containing 6 to 20 carbon atoms, such as phenyl and xylyl;

$X^⊖$ is an anion which does not adversely affect the desired coupling action and does not adversely affect the oxoindolizinium or oxoindolizine dyes, such as $CF_3SO_3^⊖$, $Br^⊖$ and $BF_4^⊖$.

Many oxoindolizine dyes according to the invention are formed by the reaction of a phenolic coupler with an appropriate oxoindolizine. Examples of useful oxoindolizine dyes that are formed by reaction of phenolic couplers with a suitable indolizinone are represented by the formulas:

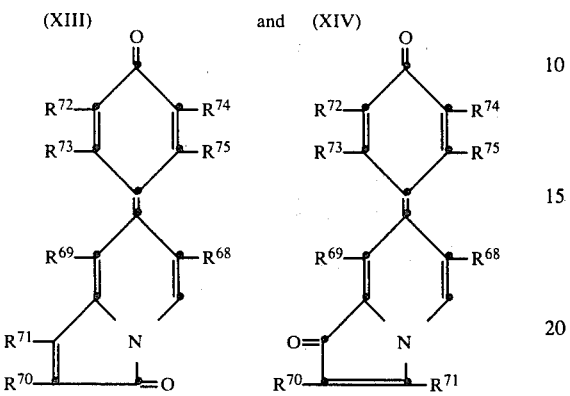

wherein:

$R^{68}$ is hydrogen or a substituent that does not adversely affect desired dye properties, such as alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine or chlorine;

$R^{69}$ is hydrogen or a substituent that does not adversely affect desired dye properties, such as chlorine, bromine or alkyl containing 1 to 18 carbon atoms, such as methyl, ethyl, propyl and dodecyl; $R^{70}$ and $R^{71}$ are individually alkyl, such as alkyl containing 1 to 18, preferably 1 to 10 carbon atoms, such as methyl, ethyl, propyl and decyl or aryl containing 6 to 20 carbon atoms, such as phenyl, tolyl, xylyl, methoxyphenyl, 4-t-butylphenyl, anisyl, naphthyl and methoxynaphthyl;

$R^{72}$ and $R^{73}$ are individually hydrogen, alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen, including chlorine, fluorine, bromine and iodine; and alkoxy containing 1 to 18 carbon atoms, such as methoxy, ethoxy and propoxy; or $R^{72}$ and $R^{73}$ together represent the atoms necessary to complete a benzo group which is unsubstituted or substituted by at least one of the groups given for $R^{17}$; and $R^{74}$ and $R^{75}$ are individually hydrogen; hydroxy; alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen, including chlorine fluorine bromine and iodine; and alkoxy containing 1 to 18 carbon atoms, such as methoxy, ethoxy and propoxy.

Examples of useful oxoindolizine dyes prepared from phenolic couplers are those in which the phenolic couplers are resorcinolic couplers. Resorcinolic couplers form compounds wherein $R^{75}$ is hydroxy.

Examples of indolizinone dyes prepared from phenolic couplers are as follows:

1,2-diphenyl-7-(4-oxo-2-hydroxy-1-phenylidene)-3(7H)-indolizinone

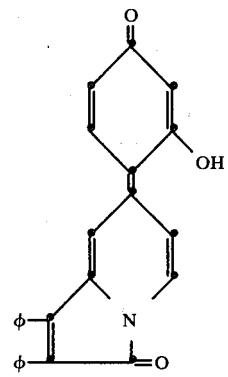

1,2-diphenyl-7-(4-oxo-1-naphylidene)-3(7H)-indolizinone

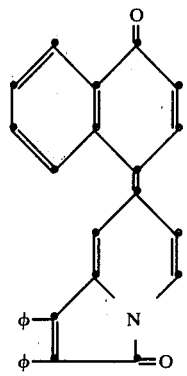

1,2-diphenyl-6-methyl-7-(4-oxo-1-phenylidene)-3(7H)-indolizinone

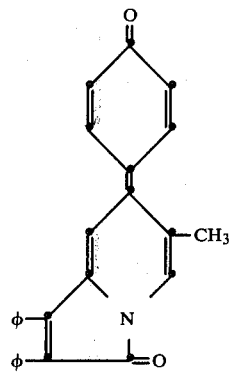

2,3-diphenyl-6-formyl-7-(4-oxo-1-phenylidene)-1-(7H)-indolizinone

-continued

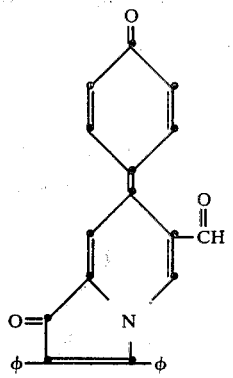

6-diethylaminocarbonyl-2,3-diphenyl-(4-
oxo-1-phenylidene)-1(7H)-indolizinone

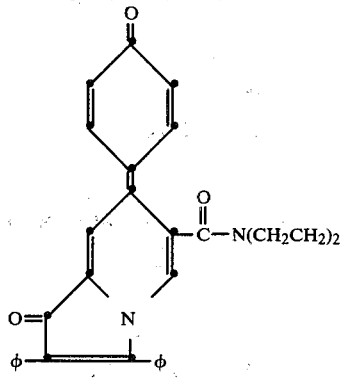

1,2-diphenyl-6-ethyl-7-(4-oxo-1-phenylidene)-
3(7H)-indolizinone

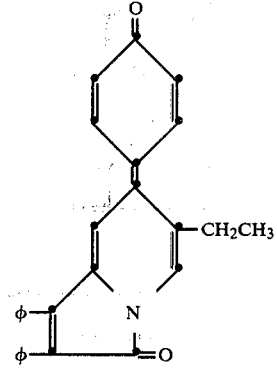

6-cyanomethyl-1,2-diphenyl-7-(4-oxo-1-
phenylidene)-3(7H)-indolizinone

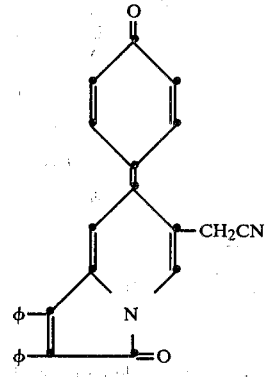

1,2-diphenyl-6-(3-hydroxypropyl)-7-(4-oxo-
1-phenylidene)-3(7H)-indolizinone

-continued

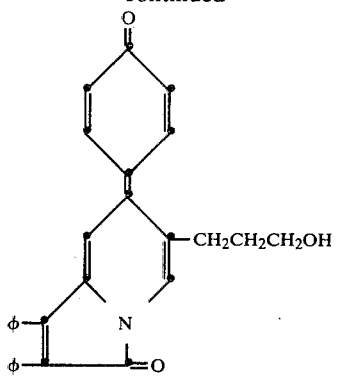

1,2-diphenyl-6-ethoxycarbonylmethyl-7-(4-
oxo-1-phenylidene)-3(7H)-indolizinone

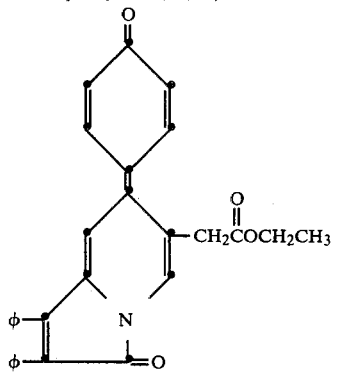

6,8-dimethyl-1,2-diphenyl-7-(4-oxo-1-
phenylidene)-3(7H)-indolizinone

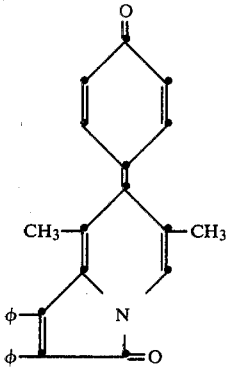

2,3-diphenyl-6-methylaminocarbonyl-7-(4-
oxo-1-phenylidene)-1(7H)-indolizinone

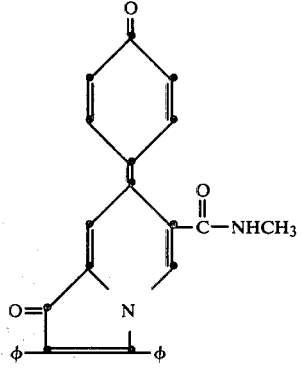

2,3-diphenyl-6-methoxycarbonyl-7-(4-oxo-
1-phenylidene)-1(7H)-indolizinone

-continued

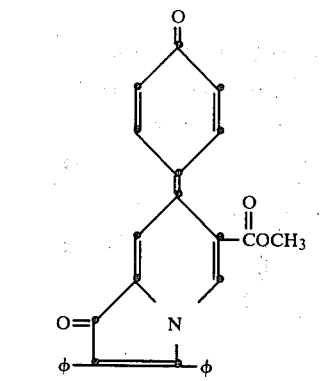

2,3-diphenyl-6-[2-methyl-2-(3-pyridyl)-
propionyl-7-(4-oxo-1-phenylidene)]-1(7H)-
indolizinone

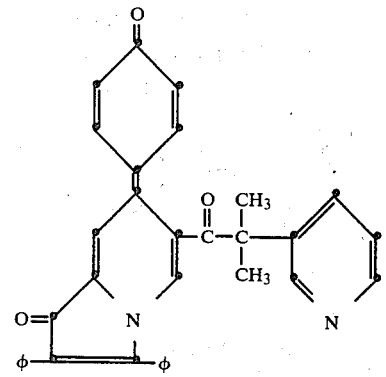

1,2-bis{6,6'-[2,3-diphenyl-7-(4-oxo-1-
phenylidene)-1(7H)-indolizinonyl]}-3-
methyl-1-oxopropane

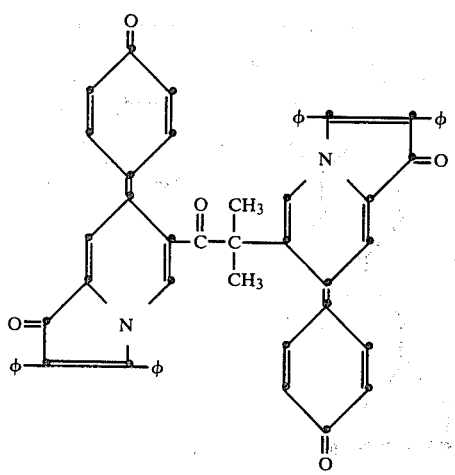

6-acetyl-2,3-diphenyl-7-(4-oxo-phenyl-
idene)-1(7H)-indolizinone

-continued

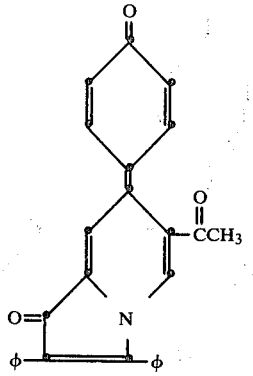

6-benzyl-1,2-diphenyl-7-(4-oxo-1-phenyl-
idene)-3(7H)-indolizinone

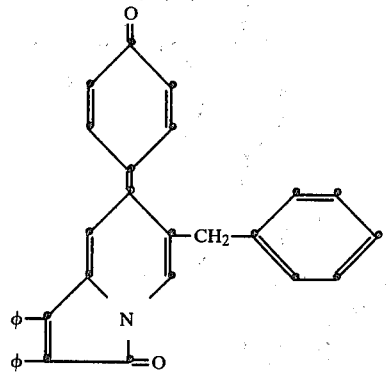

6-chloro-1,2-diphenyl-7-(4-oxo-1-phenyl-
idene)-3(7H)-indolizinone

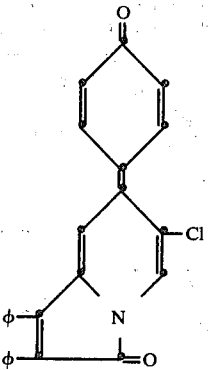

6-cyano-2,3-diphenyl-7-(4-oxo-1-phenyl-
idene)-1(7H)-indolizinone

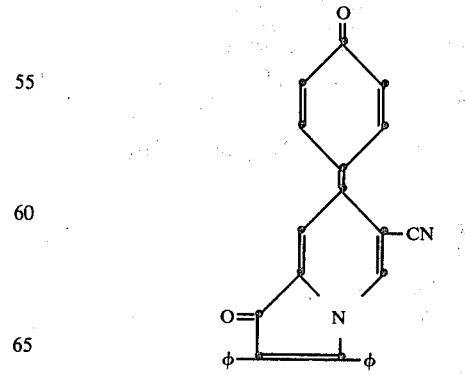

6-(4-azastyryl)-1,2-diphenyl-7-(4-oxo-
1-phenylidene)-3(7H)-indolizinone 2,3-diphenyl-7-(2-hydroxy-4-oxo-3-pival-
amido-1-phenylidene)-1(7H)-indolizinone

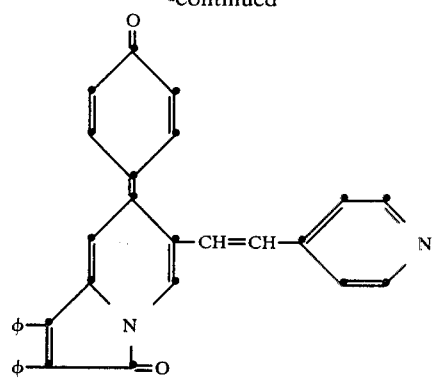

7-[3-(4-tert-butylbenzamido)-2-hydroxy-4-
oxo-1-phenylidene]-1,2-diphenyl-6-[2-(4-
pyridyl)-1-ethenyl]-3(7H)-indolizinone

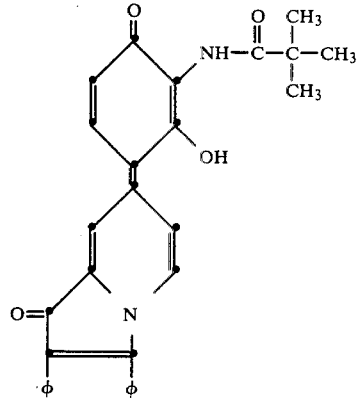

7-[3-(4-tert-butylbenzamido)-2-hydroxy-
4-oxo-1-phenylidene]-2,3-diphenyl-6-(3-
hydroxypropyl)-1(7H)-indolizinone

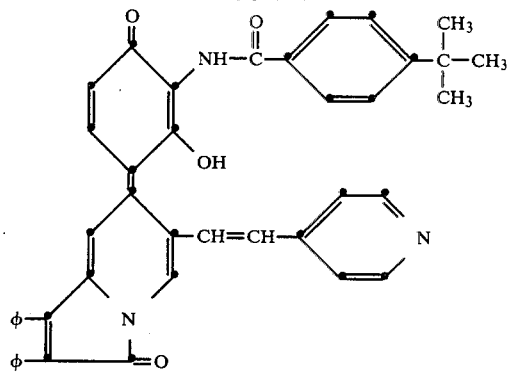

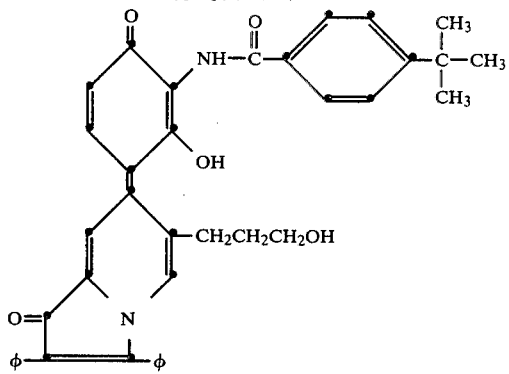

7-[3-(4-tert-butylbenzamido)-2-hydroxy-
4-oxo-1-phenylidene]-6-carbomethoxy-2,3-
diphenyl-1(7H)-indolizinone

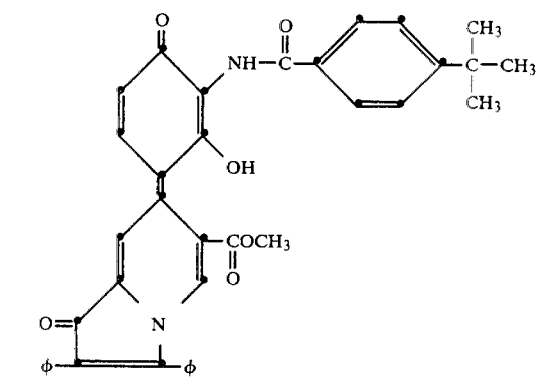

7-[3-(4-tert-butylbenzamido)-2-hydroxy-4-
oxo-1-phenylidene]-2,3-diphenyl-6-methyl-
carbamyl-1(7H)-indolizinone

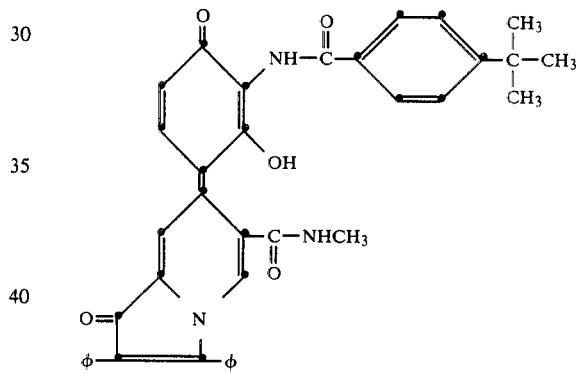

7-[3-(4-tert-butylbenzamido)-2-hydroxy-4-
oxo-1-phenylidene]-2,3-diphenyl-6-methyl-
1(7H)-indolizinone

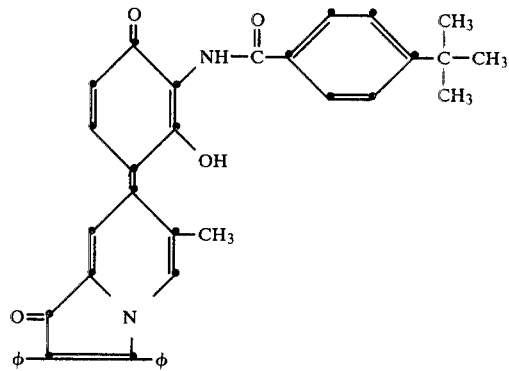

7-[3-(4-tert-butylbenzamido)-2-hydroxy-4-
oxo-1-phenylidene]-6,8-dimethyl-1,2-
diphenyl-3(7H)-indolizinone

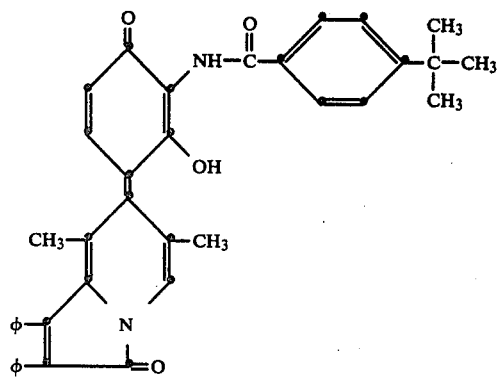

7-[3-(4-tert-butylbenzamido)-2-hydroxy-4-oxo-1-phenylidene]-6-diethylcarbamyl-2,3-diphenyl-1(7H)-indolizinone

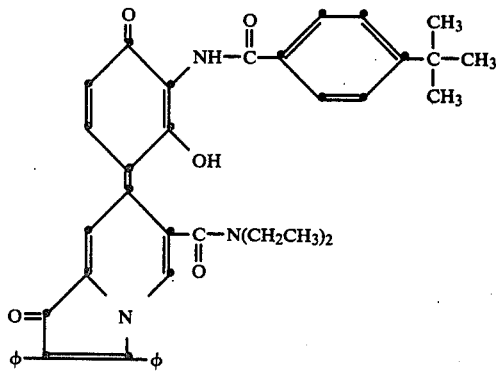

6-benzyl-7-[3-(4-tert-butylbenzamido)-2-hydroxy-4-oxo-1-phenylidene]-1,2-diphenyl-3(7H)-indolizinone

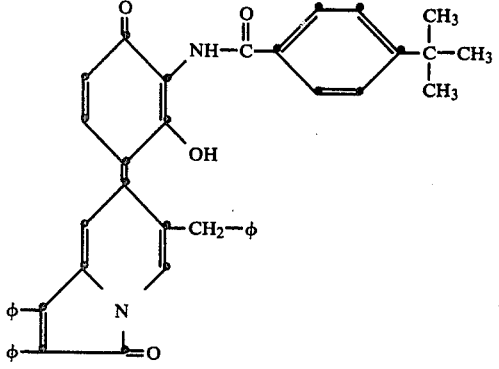

1,2-bis-{6,6'-{7-[3-(4-tert-butyl-benzamido)-2-hydroxy-4-oxo-1-phenyl-idene]}-2,3-diphenyl-1(7H)-indolizinonyl}-2-methyl-1-oxo-propane

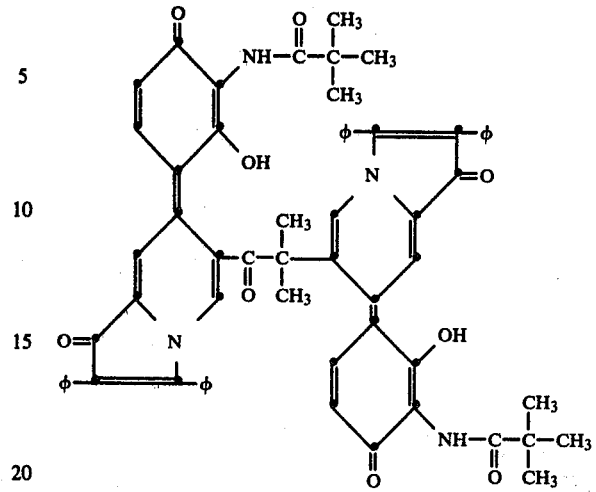

2,3-diphenyl-7-[3-(4-tert-butylbenzamido)-2-hydroxy-4-oxo-1-phenylidene]-1(7H)-indolizinone

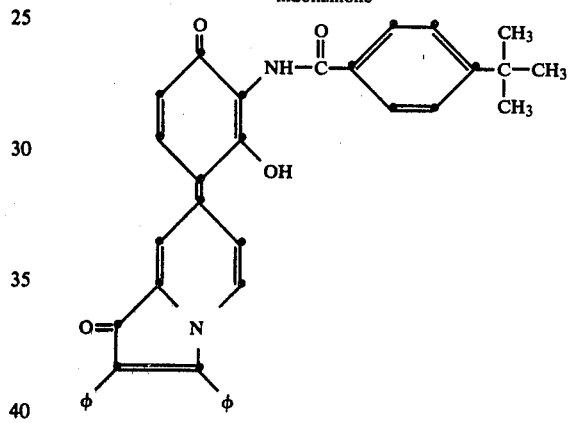

7-[3,5-di-tert-butyl-4-oxo-1-phenylidene]-1,2-di-(4-methoxyphenyl)-3(7H)-indolizinone

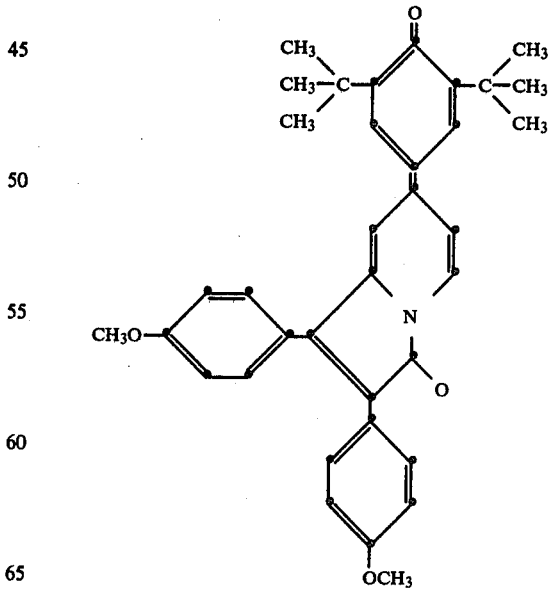

7-[3,5-di-tert-butyl-4-oxo-1-phenylidene]-2,3-di-n-propyl-1(7H)-indolizinone

-continued

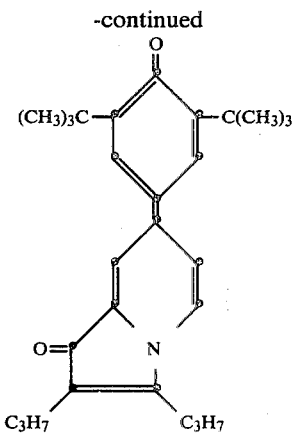

Examples of oxoindolizinium dyes according to the invention are formed from reaction of an aniline coupler with an oxoindolizine compound. Examples of such oxoindolizinium dyes formed from aniline couplers are represented by the formulas:

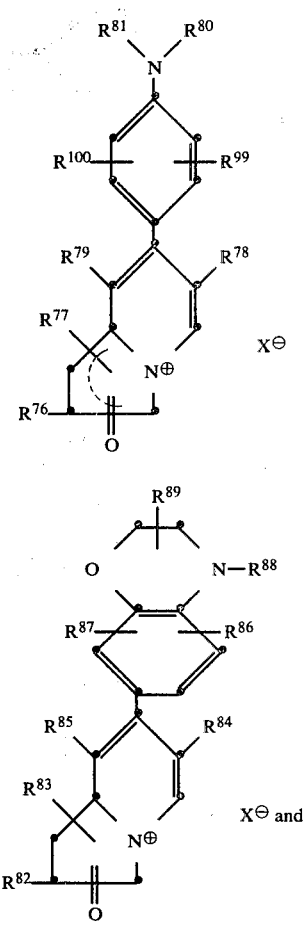

(XV)

(XVI)

$X^{\ominus}$ and

-continued

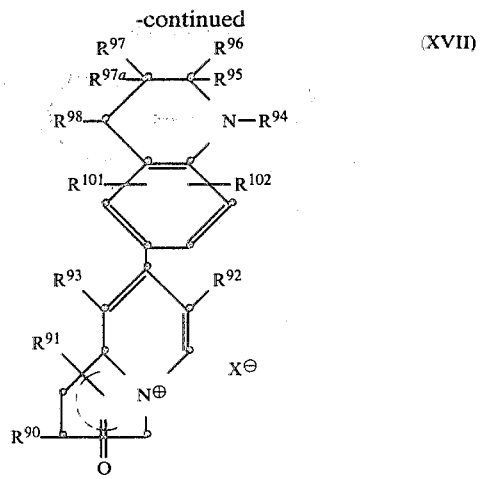

(XVII)

wherein $R^{76}$, $R^{77}$, $R^{82}$, $R^{83}$, $R^{90}$ and $R^{91}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl-(2-phenylvinyl); alkyl containing 1 to 20 carbon atoms, such as methyl, ethyl, propyl, decyl and eicosyl; or $R^{76}$ and $R^{77}$, $R^{82}$ and $R^{83}$, $R^{90}$ and $R^{91}$ together represent the carbon atoms necessary to complete a cyclic structure, such as 2,3-pentamethylene;

$R^{78}$, $R^{84}$ and $R^{92}$ are individually hydrogen, alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms such as carbomethoxy, carboethoxy and carbobutoxy; aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine;

$R^{79}$, $R^{85}$ and $R^{93}$ are individually hydrogen; chlorine; bromine; or, alkyl containing 1 to 18 carbon atoms, such as methyl, ethyl, propyl and dodecyl;

$R^{80}$, $R^{81}$, $R^{88}$ and $R^{94}$ are individually hydrogen or substituents that do not adversely affect the desired indolizinium dye, such as alkyl containing 1 to 20 carbon atoms, such as methyl, ethyl, propyl, decyl, and eicosyl; cycloalkyl, such as cycloalkyl containing 6 to 20 carbon atoms; straight or branched chain alkenyl containing 2 to 10 carbon atoms; or $R^{80}$ and $R^{81}$ together represent the atoms necessary to complete a 5- or 6-member heterocyclic ring with the nitrogen atom to which they are bonded, such as atoms completing a pentamethylene, ethyleneoxyethylene or ethylenesulfonylethylene group which forms a ring, or a julolidyl group;

$R^{99}$, $R^{100}$, $R^{86}$, $R^{87}$, $R^{101}$ and $R^{102}$ are individually hydrogen; fluorine; chlorine; bromine; alkyl containing 1 to 6 carbon atoms; cycloalkyl containing 5 to 12 carbon atoms; alkoxy containing 1 to 4 carbon atoms; phenoxy; alkylthio, such as alkylthio containing 1 to 4 carbon atoms; arylthio, such as arylthio containing 6 to 20 carbon atoms; and groups represented by the formula —NH—$XR^{36}$ in which X is —CO—, —COO— or —$SO_2$—, wherein $R^{36}$ is as defined; and $R^{89}$, $R^{95}$, $R^{96}$, $R^{97}$, $R^{97a}$ and $R^{98}$ are individually hydrogen and alkyl containing 1 to 6 carbon atoms; and $X^{\ominus}$ is an anion as defined, such as $CF_3SO_3^{\ominus}$, $BF_4^{\ominus}$ and $Br^{\ominus}$.

Many useful oxoindolizine dyes according to the invention are formed from the reaction of an active methylene coupler with a suitable oxoindolizinone compound. Especially useful oxoindolizines are dyes formed from the reaction of ketomethylene couplers, methylpyrylium couplers and methylindolizinium couplers with appropriate oxoindolizine compounds. Examples of useful oxoindolizine dyes formed from active methylene couplers are represented by the formula:

(XVIII) and (XVIIIA)

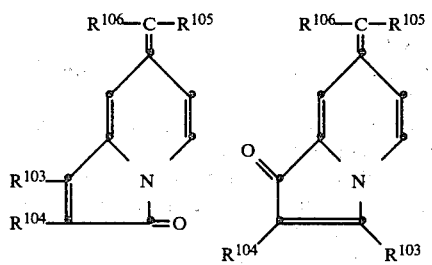

wherein:

$R^{103}$ and $R^{104}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl-(2-phenylvinyl); alkyl containing 1 to 20 carbon atoms, such as methyl, ethyl, propyl, decyl and eicosyl; or $R^{103}$ and $R^{104}$ together represent the carbon atoms necessary to complete a cyclic structure, such as 2,3-pentamethylene;

$R^{105}$ and $R^{106}$ are individually electronegative groups, such as aryl containing 6 to 20 carbon atoms, such as phenyl and naphthyl; cyano; acyl containing 2 to 18 carbon atoms, such as acetyl, propionyl and butyryl; carboalkoxy containing 2 to 18 carbon atoms, such as carbomethoxy, carboamyloxy and carbobutoxy; aminocarbonyl containing 1 to 18 carbon atoms such as unsubstituted aminocarbonyl, methylaminocarbonyl, dimethylaminocarbonyl and ethylaminocarbonyl; and $R^{105}$ is alternatively hydrogen.

Examples of indolizinone dyes formed from active methylene couplers are as follows:

7-(diacetylmethylidene)-1,2-diphenyl-3(7H)-indolizinone

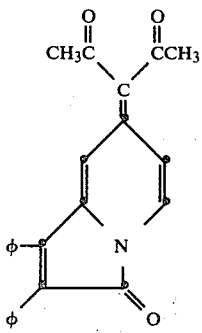

7-(dibenzoylmethylidene)-2,3-diphenyl-

-continued
1(7H)-indolizinone

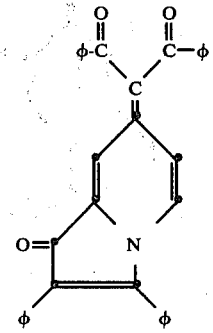

7-(anilinocarbonyl benzoylmethylidene)-2,3-diphenyl-1(7H)-indolizinone

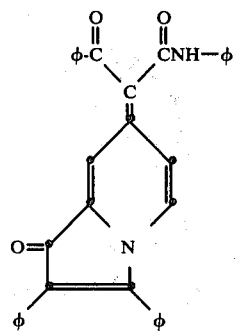

6-cyano-7-(diacetylmethylidene)-2,3-diphenyl)-1(7H)-indolizinone

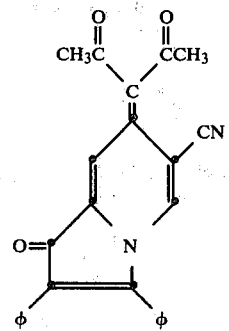

7-(dicyanomethylidene)-2,3-diphenyl-1(7H)-indolizinone

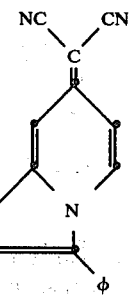

7-(1-cyano-1-phenylmethylidene)-1,2-diphenyl-3(7H)-indolizinone

-continued

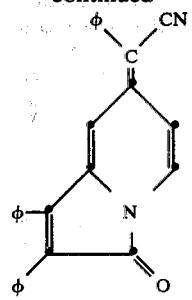

7-(1-aminocarbonyl-1-phenylmethylidene)-
2,3-diphenyl-1(7H)-indolizinone

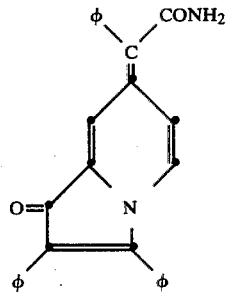

7-(dicarboethoxymethylidene)-2,3-diphenyl-
1(7H)-indolizinone

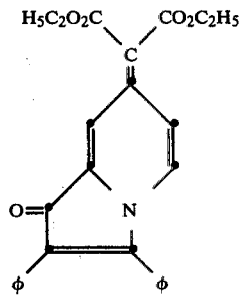

2,3-diphenyl-7-(2,2-dimethyl-4,6-dioxo-
1,3-dioxanylidene)-1(7H)-indolizinone

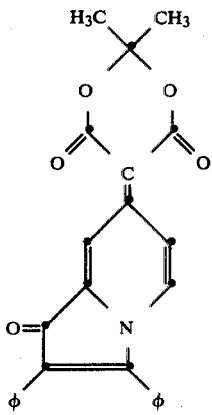

Other examples of oxoindolizinium dyes formed from active methylene couplers are represented by the formula:

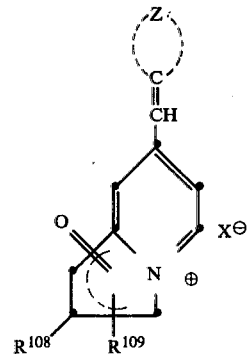 (XIX)

wherein
$X^{\ominus}$ is as defined;
$R^{108}$ and $R^{109}$ are individually the same as $R^{103}$ and $R^{104}$; and Z represents the atoms necessary to complete an organic chromophore, such as the carbon, hydrogen, oxygen and nitrogen atoms necessary to complete a heterocyclic group, such as a pyranylidene, indolizinylidene, thiopyranylidene, selenopyranylidene, coumarinylidene, or pyrazolinonylidene group.

Examples of oxoindolizinium dyes formed from such active methylene couplers are as follows:

2,3-diphenyl-7-[(2,6-diphenyl-4-
pyranylidene)methyl]-1-oxoindolizinium
perchlorate

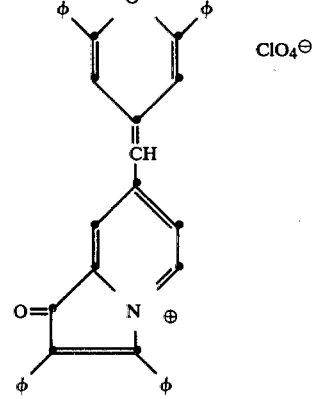

2,3-diphenyl-7-[(2,3-diphenyl-7-1(7H)-
indolizinonylidene)methyl]-1-indoli-
zinonium trifluoromethane sulfonate

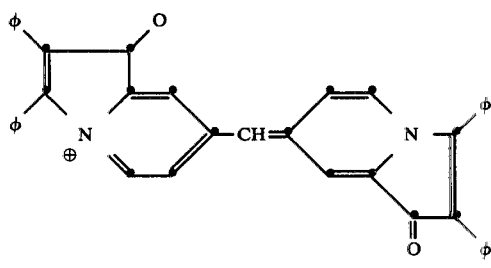

2,3-diphenyl-7-[(2,6-diphenyl-4-thio-
pyranylidene)methyl]-1-indolizinonium
trifluoromethane sulfonate -continued

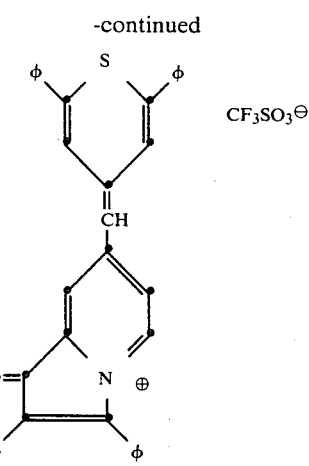 CF₃SO₃⁻

Another class of oxoindolizine dyes according to the invention is represented by the formula:

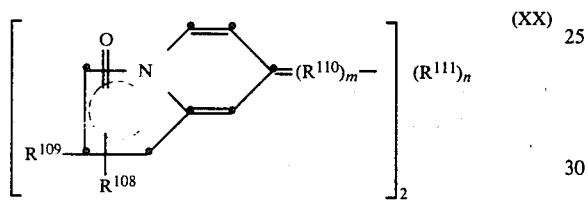 (XX)

wherein:

$R^{108}$ and $R^{109}$ are individually aryl containing 6 to 14 carbon atoms, such as phenyl, naphthyl and anthryl; or, alkyl containing 1 to 20 carbon atoms, such as methyl, ethyl, butyl and eicosyl;

$R^{110}$ is CH, phenylene or naphthylene;

$R^{111}$ is ethane, phenylene or naphthylene; and n and m are individually 0 or 1.

In oxoindolizine dyes according to the formula containing $R^{110}$ and $R^{108}$, the oxoindolizine moiety represents a group completing an organic chromophore to produce the desired dye. Examples of such compounds are:

1,2-bis[7-(1,2-diphenyl-3(7H)-indolizinonylidene)]ethane

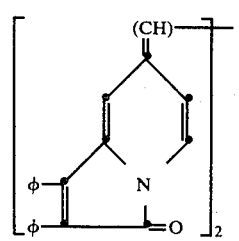

1,4-bis[7-(1,2-diphenyl-3(7H)-indolizinonylidene)]-2,5-cyclohexadiene

-continued

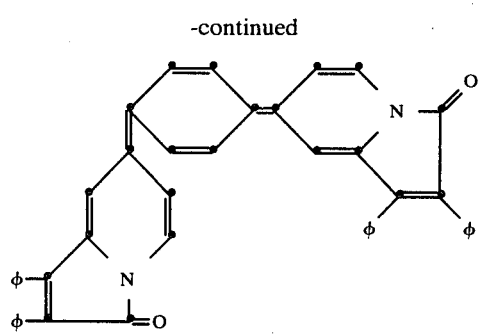

1,4-bis[7-(1,2-diphenyl-3(7H)-indolizinonylidene)]-2,3-benzo-2,5-cyclohexadiene

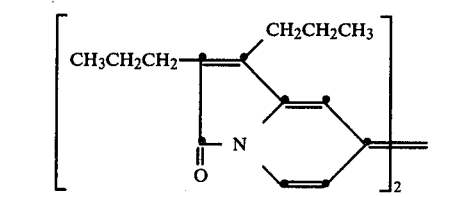

7,7'-bis[1,2-di-n-propyl-3(7H)-indolizonylidene]

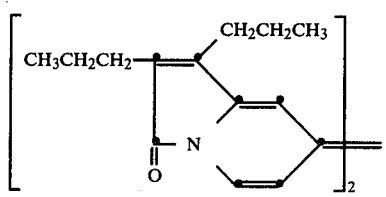

7,7'-bis-[1,2-pentamethylene-3(7H)-indolizonylidene]

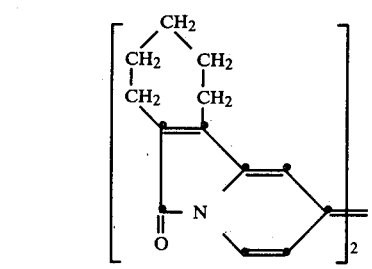

1,2-bis-[2,3-di-(4-methoxyphenyl)-1(7H)-indolizinonylidene]ethane

-continued

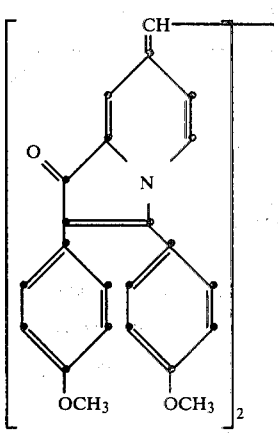

Examples of other dyes within the above structures (I) and (II) are as follows:

N—benzyl-4-{7-[2,3-di(4-methoxyphenyl)-3-indolizinolyl]}pyridinium bromide

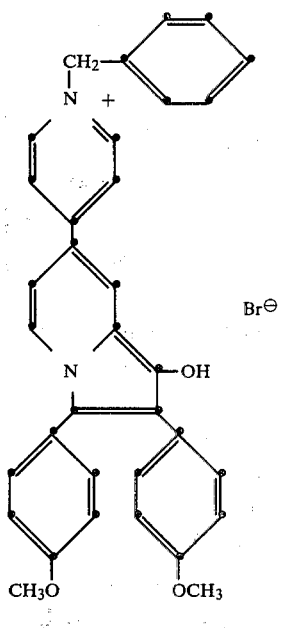

7-[4-(N—benzylpyridylidene)]-2,3-diphenyl-1-hydroxy indolizinium chloride

-continued

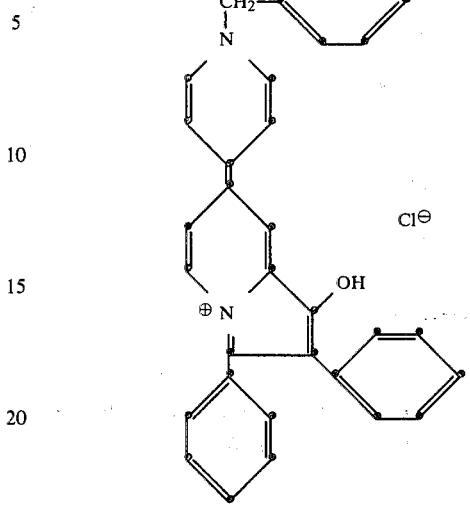

7-[4-(N—benzylpyridylidene)]-2,3-diphenyl-1-indolizinone

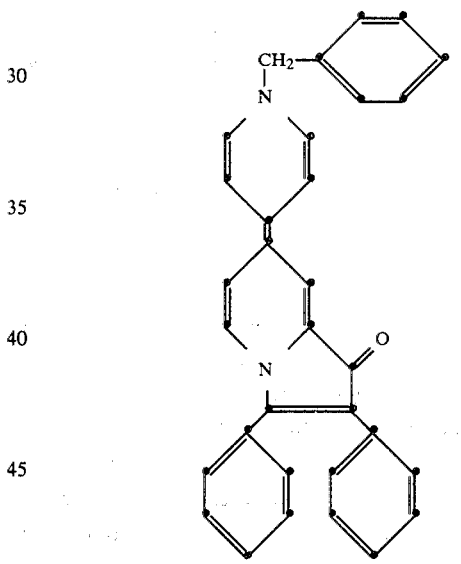

A further class of dye according to the invention is represented by the formula:

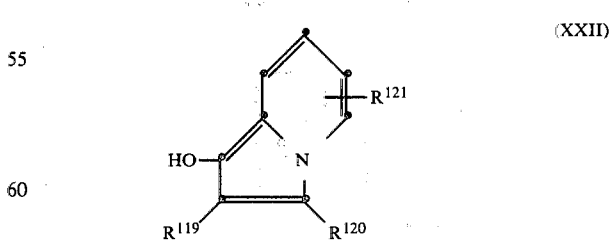

(XXII)

wherein:

$R^{119}$ and $R^{120}$ are individually aryl containing 6 to 14 carbon atoms, such as phenyl and naphthyl; or, alkyl containing 1 to 20 carbon atoms, such as methyl, ethyl, propyl, decyl and eicosyl;

$R^{121}$ is cyano, carboxy, formyl, acyl containing 2 to 18 carbon atoms, such as acetyl, propionyl and lauroyl; carboalkoxy containing 2 to 18 carbon atoms, such as carbomethoxy, carboethoxy and carbobutoxy; or aminocarbonyl containing 1 to 19 carbon atoms, such as unsubstituted aminocarbonyl, methylaminocarbonyl and dimethylaminocarbonyl.

The compounds in this class are shown in the enol form, rather than the keto form. Examples of compounds within this class are as follows:

7-cyano-2,3-diphenyl-1-indolizinol

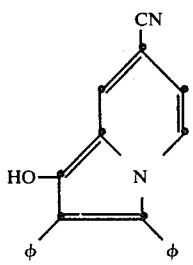

7-formyl-2,3-di-(4-methoxyphenyl)-1-indolizinol

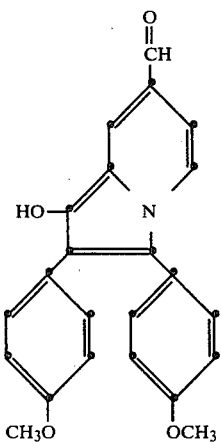

6-aminocarbonyl-2,3-diphenyl-1-indolizinol

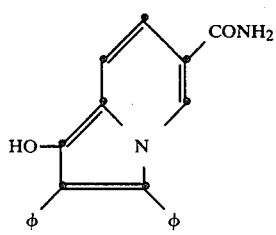

8-carboethoxy-2,3-diphenyl-1-indolizinol

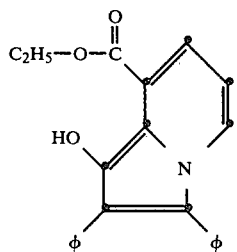

7-carboxy-2,3-diphenyl-1-indolizinol

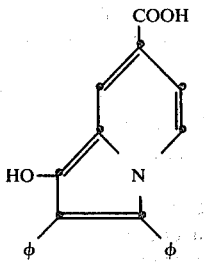

The oxoindolizine and oxoindolizinium dyes according to the invention are formed in a photographic material by reacting, such as by heating, (A) a suitable pyridine compound with (B) a photosensitive cyclopropenone. The resulting oxoindolizine or oxoindolizinium compound is a dye or a dye is produced from the resulting oxoindolizine or oxoindolizinium compound by reacting the product with an appropriate color-forming compound, such as a color-forming coupler. Such a method is illustrated by the preparation of dyes represented by formulas I and II above comprising the steps:

(1) heating (A) a pyridine compound represented by the formula:

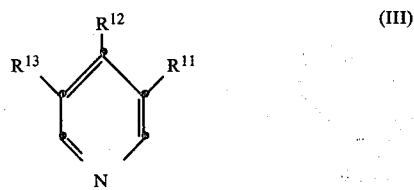

(III)

with (B) a photosensitive cyclopropenone represented by the formula:

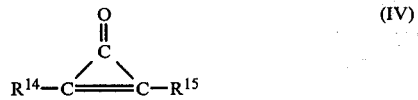

(IV)

wherein $R^{11}$, $R^{12}$, $R^{13}$, $R^{14}$ and $R^{15}$ are as defined above; and, (2) reacting the resulting product from (1) with a color-forming compound, such as a color-forming coupler, in the presence of an oxidant agent that catalyzes formation of a dye according to the invention. Some of the compounds produced in step (1) are dyes which absorb in the visible region of the electromagnetic spectrum.

Optimum methods for preparation of dyes according to the invention in a photographic material vary, depending upon the desired dye, particular starting material, such as the particular cyclopropenone, particular color-forming coupler, particular pyridine compound, solvents present, processing temperature, concentration of reactants, and catalysts present. The cyclopropenone and pyridine compounds are generally mixed in about stoichiometric cocentrations; however, it is often useful to mix the reactants with an excess of the pyridine compound to provide better yields or different isomers.

An imaging medium is most useful which comprises a solvent for the reactants. Useful solvents include, for example, pyridine, chlorinated hydrocarbons, such as methylene chloride and chlorobenzene, toluene, dioxane, and tetrahydrofuran. The optimum temperature is influenced by the choice of solvent, the particular reactants, the desired dye, and other described factors.

When a dye according to the invention is formed in a photographic material by the reaction of a cyclopropenone with a pyridine compound and suitable color-forming compound, such as a color-forming coupler, it is generally preferred that the reaction be carried out in chemical association with an appropriate oxidant, such as elemental iodine, copper bromide, copper acetate, benzoyl peroxide or copper acetylacetonate. The concentration of oxidant that is useful will vary, depending upon the particular reactants, processing conditions, desired dye, and reaction medium. An oxidant is especially useful in the reaction of a cyclopropenone with a pyridine compound and an active methylene coupler.

An example of a process according to the invention is the preparation of an oxoindolizine dye image comprising an oxoindolizine dye represented by the formula:

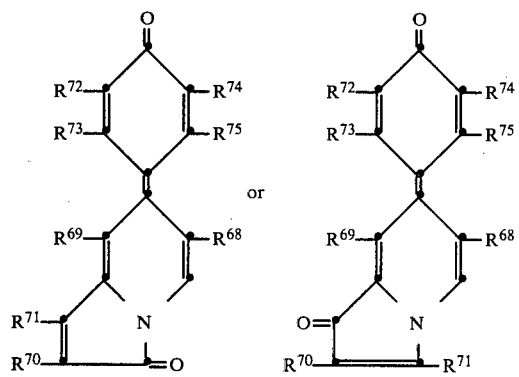

wherein:

$R^{68}$, $R^{69}$, $R^{70}$, $R^{71}$, $R^{72}$, $R^{73}$, $R^{74}$ and $R^{75}$ are as defined above; comprising the steps:

(1) reacting, such as by heating a mixture of a pyridine compound, such as a pyridine compound as defined by structure (III), with a cyclopropenone represented by the formula:

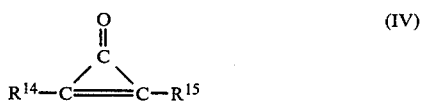

(IV)

wherein $R^{14}$ and $R^{15}$ are as defined above; and (2) heating the product from (1) with a phenolic color-forming coupler represented by the formula:

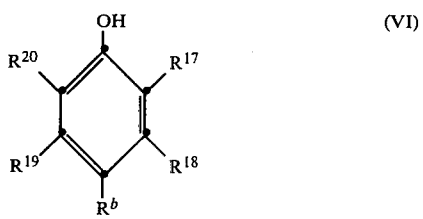

(VI)

wherein $R^{17}$, $R^{18}$, $R^{19}$ and $R^{20}$ and $R^b$ are as defined above, in the presence of an inorganic oxidant that catalyzes the formation of the oxoindolizine dye.

Useful inorganic oxidants are, for example, oxygen, copper acetate, copper chloride and iodine.

Another process according to the invention comprises heating an aniline coupler, as described, in place of a phenolic color-forming coupler, with an oxoindolizine.

The reactions according to the invention for forming an oxoindolizine or oxoindolizinium dye take place in the unexposed areas of an imaging element. The cyclopropenone is inactivated in the exposed areas, which results in no oxoindolizine or oxoindolizinium dye formation in the exposed areas. Based on such a reaction, an especially useful embodiment of the invention is a photographic material, preferably a photothermographic material, comprising a photosensitive cyclopropenone, in a binder, in reactive association with a pyridine compound that reacts with the cyclopropenone to form an oxoindolizine or oxoindolizinium compound.

A binder is useful in a photothermographic material according to the invention. The binder is preferably a film-forming compound which enables the imaging material to be coated on a suitable support. Most useful binders are those which are resistant to undesired changes in physical and chemical properties at processing temperatures, such as temperatures above about 80° C. The binder is preferably dimensionally stable at varying humidities and processing temperatures. Useful binders include synthetic polymeric materials which do not adversely affect the reaction between pyridine and cyclopropenone, such as cellulose acetate butyrate, poly(vinyl butyral), polyvinyl alcohol, polyvinyl chloride, polysulfonamide-styrene copolymers, copolymers of butadiene and styrene, polyisoprene and polysulfonamide binders. Gelatino binders are not especially useful because they tend to interfere with the reaction between cyclopropenone and pyridine.

Imaging materials according to the invention are also useful in a photographic element in combination with photographic materials not based on the reaction of cyclopropenone with a pyridine compound. For example, imaging elements according to the invention are useful which comprise a layer of a diazo or vesicular image-forming material and a layer of an imaging material according to the invention comprising a photosensitive cyclopropenone and a pyridine compound. Imaging materials according to the invention are also useful in combination with photographic silver halide materials which do not adversely affect the desired reaction of the cyclopropenone compound with the pyridine compound. An example of an imaging element comprises a layer of a photographic silver halide material and a layer of an imaging material comprising a photosensitive cyclopropenone and a pyridine compound. Photographic silver halide materials which are useful in such elements are described in, for example, Research Disclosure, (published by Industrial Opportunities Ltd.; Homewell, Havant; Hampshire, PO9 1EF, United Kingdom), November 1979, Item No. 18716; Research Disclosure, August 1979, Item No. 18431; Research Disclosure, December 1978, Item No. 17643; and Research Disclosure, June 1978, Item No. 17029. Useful photographic silver halides in such materials include, for example, silver chloride, silver bromide, silver bromoiodide, silver chlorobromoiodide and mixtures thereof.

The photographic materials comprising photographic silver halide according to the invention, if desired, also contain addenda which do not adversely affect the desired properties of the materials, such as antifoggants, tone modifiers, chemical sensitizers, hardeners, matting agents, brighteners, absorbing and filter dyes, development modifiers, spectral sensitizers and coating aids, as described in *Research Disclosure*, June, 1978, Item 17029, and December, 1978, Item 17643.

Many supports are useful for a photographic element according to the invention. Useful supports include those which are resistant to adverse changes in structure, and do not adversely affect the sensitometric properties of the described photothermographic materials at processing temperatures. Useful supports include cellulose ester, poly(vinyl acetal), poly(ethylene terephthalate), polycarbonate, and related films and resinous materials, as well as glass, paper and metal. A flexible support is generally most useful, especially a flexible paper support.

The photographic materials according to the invention are coated by means of coating procedures known in the photographic art. Such procedures are described in *Research Disclosure*, December, 1978, Item No. 17643.

The pyridine compound and cyclopropenone compound, as well as the color-forming coupler, are in a location in the photographic material which enables the desired interaction to form a dye image upon processing. Each of the compounds is useful in one or more layers of a photographic element according to the invention. For example, the cyclopropenone compound and color-forming coupler are useful in one layer with a contiguous layer containing a pyridine compound. The pyridine compound and cyclopropenone compound, as well as the color-forming coupler, are in, for example, a photothermographic material in a location which enables the desired interaction upon heating the photothermographic material to processing temperature. It is important that the compounds be in a location with respect to each other which enables the desired interaction produced upon processing to enable formation of the desired dye. The term "in reactive association" herein means that the reactants are in such a location enabling such a desired interaction to form a desired dye upon processing.

Many silver halide developing agents are useful in a photographic material according to the invention which comprises silver halide. Combinations of silver halide developing agents are useful. Useful silver halide developing agents include, for example those described in *Research Disclosure*, June, 1978, Item No. 17029. It is important that the developing agent not adversely affect the desired interaction between the cyclopropenone compound and the pyridine compound in the photothermographic material.

The optimum concentration of each component in a photographic material according to the invention depends upon such factors as the desired image, processing conditions, and particular components of the photographic material. In a photographic element according to the invention, useful concentrations are generally within the following ranges:

(a) cyclopropenone: 0.1 to 2.0;
(b) pyridine compound: 0.2 to 4.0, preferably 1.0 to 2.0; and
(c) color-forming coupler: 0.2 to 4.0, preferably 1.0 to 2.0 grams per square meter of support.

Exposure of a photographic material according to the invention is by means of forms of energy to which the cyclopropenone is sensitive. The photosensitive cyclopropenone is generally imagewise exposed to light. Alternatively, other forms of energy are useful, such as electron beams, x-rays, gamma rays, alpha particles and other nuclear particles. Lasers are also useful. Imagewise exposure of the photographic material is generally sufficient in time and intensity to provide an image which is developable, such as upon subsequent heating of the photothermographic material to processing temperature.

After exposure of a photographic material according to the invention, a visible image is produced by, for example, heating the photographic material to a processing temperature within the range of about 80° C. to about 150° C. until a dye image is formed. An image is generally produced by heating the photographic material to a processing temperature within the range of about 80° C. to about 150° C. for about 0.3 to about 60 seconds, such as about 1 to about 10 seconds.

Processing is preferably carried out under ambient conditions of pressure and humidity.

Various means are useful for heating the exposed photothermographic material according to the invention. The photothermographic material containing the exposed cyclopropenone is generally brought into contact with a simple hot plate, iron, rollers, dielectric heating means, heated drum or microwave heating means.

The following examples are included for a further understanding of the invention.

EXAMPLE 1

Photothermographic Element for Producing Red Dye Images

A dope solution was prepared containing 525 mg of poly(ethylene-co-1,4-cyclohexylenedimethyl-ene-1-methyl-2,4-benzenedisulfonamide) (binder), 400 mg of 1-methyl-4-(4-pyridyl)pyridinium-para-toluene-sulfonate (pyridine compound) and 9.980 g of 2-methoxyethanol (solvent). The polysulfonamide binder and quaternary salt (pyridine compound) were dissolved in the 2-methoxyethanol by gentle agitation at room temperature (19° C.). A clean lacquer solution resulted. The dope was coated on a poly(ethylene terephthalate) film support at a wet coating thickness of 0.125 mm. The coating was dried by heating the material to about 24° C. (about 75° F.) for 30 minutes in a stream of air.

A second dope was prepared by dissolving 525 mg of poly(styrene-co-butadiene) (KRO-3 TM, which is a trade name of and available from Phillips Petroleum Company, U.S.A.), in 9.98 g of toluene with 40 mg of 1-phenyl-2-(para-methoxyphenyl)cyclopropenone (photosensitive cyclopropenone compound). Solution was produced by stirring at 22° C. for several hours. A clear lacquer solution resulted. The resulting dope containing the photosensitive cyclopropenone was coated directly over the first layer containing the pyridine compound. A wet coating thickness of 0.125 mm was applied. The resulting composite two-layer element was dried by warming the material to 45° C. for 30 minutes. The resulting photothermographic element according to the invention was exposed to a 250 watt mercury lamp for 20 seconds at a distance of 3 inches through a step wedge to produce a developable image in the photothermographic element. The desired dye image was produced by heating the photothermographic element after exposure to 150° C. for 3 seconds on a heated aluminum block. A brilliant red dye image was formed in the film. The resulting red dye image had a maximum absorption at 535 nm. The green light image density was measured by means of a commercial densitometer. The maximum image density was 1.83, and the minimum density was 0.08.

EXAMPLE 2

Photothermographic Element Producing a Blue Dye Image

A coating solution was prepared by dissolving 0.500 g of the polysulfonamide binder as described in Example 1 and 500 mg of 4-(4-azastyryl)-1-methyl-pyridinium para-toluenesulfonate (pyridine compound) in 10 g of 2-methoxyethanol (solvent). Solution was produced by stirring at room temperature (19° C.). A clear lacquer solution resulted. The resulting dope solution was coated on a poly(ethylene terephthalate) film support by means of a doctor blade to produce a wet coating thickness of 0.125 mm. The resulting coating was dried by heating the coating to about 24° C. (about 75° F.) for 30 minutes in a stream of rapidly moving air.

A second solution was prepared by dissolving 25 mg of phenylanisyl cyclopropenone and 0.50 g of poly(styrene-co-butadiene) resin in 10.0 g of toluene. A clear solution resulted upon stirring the mixture for 3 hours at room temperature (19° C.). The dope containing the photosensitive cyclopropenone was coated directly over the first layer containing the pyridine compound. A wet coating thickness of 0.125 mm was applied by means of a doctor blade. The composite two-layer photothermographic element according to the invention was dried by warming the resulting coating to about 24° C. (about 75° F.) for 30 minutes in a stream of rapidly moving air. A brilliant clear transparent film was obtained.

The resulting photothermographic element was imagewise exposed and then heated as described in Example 1. A blue dye image was formed in the film. The blue dye had a maximum absorption at 575 nm. The maximum density measured by integrated visible light on a commercial spectrophotometer was 1.50, with a minimum density of 0.08.

EXAMPLE 3

Photothermographic Element Producing a Green Image Absorbing in the Infrared Region A coating solution was prepared by dissolving 0.50 g of poly(styrene-co-butadiene) resin and 125 mg of 4,4'-dipyridylethylene (pyridine compound) in 10.0 g of toluene (solvent). A clear solution resulted upon stirring the resulting mixture at room temperature (19° C.). The coating solution was coated on a poly(ethylene terephthalate) film support containing a subbing layer. The composition containing the pyridine compound was coated at a wet coating thickness of 0.125 mm. The resulting coating was dried by heating to about 24° C. (about 75° F.) for 30 minutes. A second layer was coated over the layer containing the pyridine compound. The second layer was prepared from a coating solution produced by dissolving 0.50 g of poly(vinyl alcohol) in 9.50 g of water. The composition containing the poly(vinyl alcohol) was coated at a wet coating thickness of 0.125 mm over the first layer. The resulting composite film was dried by heating to 24° C. (about 75° F.) for 30 minutes. A top layer was then applied to the film. The top layer was prepared by coating a solution containing 125 mg of photosensitive phenylanisyl cyclopropenone and 0.50 g of poly(styrene-co-butadiene) dissolved in 10.0 g of toluene. The top layer was coated at a wet coating thickness of 0.125 mm. The resulting composite film was permitted to dry for 30 minutes at 24° C. (about 75° F.) in a rapidly moving air stream. The composite film was then imagewise exposed for 40 seconds and then heated as described in Examples 1 and 2. A dye image was produced in the film that had a maximum absorption in the infrared region of the electromagnetic spectrum at 815 nm. The image density of the resulting image was measured by integrated visible light in a commercial spectrophotometer. The maximum density of the image was 1.50, with a minimum density of 0.08.

EXAMPLE 4

One Layer Photothermographic Element

A coating solution was prepared by dissolving 0.500 g of poly(styrene-co-butadiene) resin, 40 mg of o,p-dianisylcyclopropenone (photosensitive cyclopropenone), and 40 mg of 1,2-bis(4-pyridyl)ethylene (pyridine compound) in 10.0 g of toluene. The dope was coated on a poly(ethylene terephthalate) film support at a wet coating thickness of 0.125 mm. The coating was dried by standing at 24° C. for two hours. The resulting photothermographic element was exposed to a 250 watt mercury lamp for 20 seconds at a distance of three inches through a mask to produce a developable image in the photographic element. The desired dye image was produced by heating the photothermographic element after exposure to 150° C. for 10 seconds on a heated aluminum block. An infrared dye was formed in the film with a maximum absorbtion at 830 nm. The image density in the unexposed section of the film was 2.5 at 830 nm as measured on a commercial spectrophotometer with a minimum density of 0.08. At 700 nm the maximum density was 0.95 and the minimum density was 0.09.

The following preparations of indolizinone dyes were carried out, among other reasons, to help confirm the structures of dyes which are produced in photothermographic materials.

(A) Preparation of 7,7'-(1,2-Ethane-(ε)-di-ylidene)bis-1,2-di-(4-tert-butyl-phenyl-3(7H)-indolizine Dye A solution (10 percent by weight) of 2,3-di(4-tertiarybutylphenyl) cyclopropenone, in 4-picoline (pyridine compound), was prepared containing a trace of cupric acetate (catalyst). The solution was sparged with a stream of air to provide agitation and excess oxygen. The solution was heated on a steam bath to 80° C. to 95° C. for 15 minutes. A pasty cyan-colored slurry resulted. The resulting mixture was filtered to remove excess picoline, and the colored solids washed with acetone. The solids were dried under vacuum to remove the solvent. A 25 percent yield of the desired dye was obtained based on the cyclopropenone starting material. The dye had a maximum absorption at 695 nm in chloroform solution. The structure was confirmed by mass spectroscopy, nuclear magnetic resonance, infrared spectral analysis and x-ray diffraction.

(B) Preparation of 7-(4-Pyridyl)-2,3-di-(4-methoxyphenyl)indolizinol, Benzyl Bromide Salt Equimolar amounts of benzyl bromide and 4,4'-dipyridine were dissolved in N,N-dimethyl-formamide to form approximately a 10 percent by weight solution. The solution was heated for 10 minutes on a steam bath at 95° C. to form the quaternary salt of bipyridine. The reaction mixture was cooled slightly, and an equimolar amount of 2,3-di(4-methoxyphenyl) cyclopropenone was added to the solution. The reaction mixture was heated for 15 minutes and quenched in excess cold water. A solution of 48 percent hydrobromic acid was added to the water-N,N-dimethylformamide solution to precipitate the desired dye product. The precipitated dye was removed by filtration and dried under vacuum. The dye had a maximum absorption density at 535 nm in chloroform solution. The desired dye structure was confirmed by mass spectroscopy, nuclear magnetic resonance and infrared spectral analysis.

(C) Preparation of 7-Dibenzoylmethylidene-2,3-di-(4-methoxyphenyl)-1(7H)-indolizinone A 10 percent solution of 2,3-di(4-methoxyphenyl) cyclopropenone in pyridine was refluxed under nitrogen for 15 minutes. The resulting solution was cooled slightly, and an equivalent amount of dibenzoylmethane based on the cyclopropenone was added to the green solution. The reaction mixture was refluxed for 60 minutes. The resulting reaction mixture was again cooled, and four equivalents of iodine dissolved in a small amount of pyridine was added to the reaction mixture. The mixture was further heated at 90° C. on a steam bath for 15 minutes. The bright blue solution was quenched by pouring it into cold excess dilute hydrochloric acid. The desired dye precipitated and was removed from the solution by filtering. A 95 percent yield of the desired dye was obtained based on the starting cyclopropenone. The dye was chromatographed on silica gel to provide a purified product. The maximum absorption of the dye was at 605 nm in chloroform solution. The structure of the dye was confirmed by mass spectroscopy, nuclear magnetic resonance and infrared analysis.

(D) Preparation of 7-Formyl-2,3-di(4-methoxyphenyl)-1-indolizinol

Equivalent amounts of 4-formylpyridine and 2,3-di(4-methoxyphenyl) cyclopropenone were dissolved in sufficient para-dioxane to form approximately at 10 percent solution. The mixture was refluxed at 102° C. under nitrogen for 2 hours. Sufficient water was then added to the reaction mixture to bring it to the cloud point at 80° C. The reaction mixture was then cooled to room temperature, and the product allowed to crystallize. The crystals were collected by filtration, and washed with a small amount of water. The dried crystals were the desired dye. The dye was produced in a 95 percent yield based on the input of cyclopropenone. The yellow dye had a maximum absorption of 435 nm in chloroform solution. The structure of the dye was confirmed by mass spectroscopy, nuclear magnetic resonance and infrared analysis.

The invention has been described in detail with particular reference to preferred embodiments thereof, but it will be understood that variations and modifications can be effected within the spirit and scope of the invention.

What is claimed is:

1. In a photographic element comprising a support having thereon a photosensitive cyclopropenone in binder, the improvement comprising:
   in reactive association with said cyclopropenone, a pyridine compound that reacts with said cyclopropenone to form an oxoindolizine or oxoindolizinium dye.

2. In a photographic element comprising a support having thereon a photosensitive cyclopropenone in binder, the improvement comprising:
   in reactive association with said cyclopropenone,
   (i) a pyridine compound that reacts with said cyclopropenone to form an oxoindolizine or oxoindolizinium compound, and
   (ii) a color-forming compound that reacts with said oxoindolizine or oxoindolizinium compound to form an oxoindolizine or oxoindolizinium dye.

3. A photographic element as in claim 1 or 2 wherein said pyridine compound is represented by the formula:

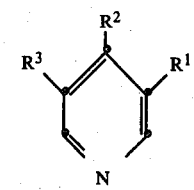

wherein:
   $R^1$ is hydrogen, alkyl containing 1 to 18 carbon atoms, acyl containing 2 to 18 carbon atoms, carboalkoxy containing 2 to 18 carbon atoms, aminocarbonyl, and acyloxy containing 2 to 18 carbon atoms;
   $R^2$ is hydrogen, alkyl containing 1 to 18 carbon atoms, acyl containing 2 to 18 carbon atoms, benzyl or pyridyl; and
   $R^3$ is hydrogen, chlorine, bromine or alkyl containing 1 to 18 carbon atoms.

4. A photographic element as in claim 1 or 2 wherein said pyridine compound consists essentially of pyridine.

5. A photographic element as in claim 1 or 2 wherein said pyridine compound consists essentially of 4-picoline.

6. A photographic element as in claim 1 or 2 wherein said photosensitive cyclopropenone consists essentially of a compound represented by the formula:

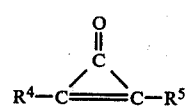

wherein
   $R^4$ and $R^5$ are individually alkyl containing 1 to 20 carbon atoms or aryl containing 6 to 20 carbon atoms.

7. A photographic element as in claim 1 or 2 wherein said photosensitive cyclopropenone consists essentially of 1-phenyl-2-(paramethoxyphenyl)cyclopropenone.

8. A photographic element as in claim 2 wherein said color-forming compound is selected from (i) phenolic, (ii) active methylene and (iii) aniline color forming couplers and combinations thereof.

9. A photographic element as in claim 1 or 2 which is a photothermographic element.

10. A photographic element comprising a support having thereon, in reactive association, phenylanisyl cyclopropenone and 1-methyl-4-(4-pyridyl)-pyridinium-p-toluenesulfonate in binder.

11. A photographic element comprising a support having thereon, in reactive association, phenylanisyl cyclopropenone and 4-azastyryl-1-methyl-pyridinium-p-toluenesulfonate in binder.

12. A photographic composition comprising (i) a photosensitive cyclopropenone, (ii) a pyridine compound that reacts with cyclopropenone to form an oxoindolizine or oxoindolizinium compound and (iii) a color-forming compound that reacts with said oxoindolizine or oxoindolizinium compound to form a dye wherein the color-forming compound is selected from (i) phenolic (ii) active methylene and (iii) aniline color-forming couplers and combinations thereof.

13. A photographic composition as in claim 12 wherein said pyridine compound is represented by the formula:

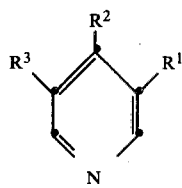

wherein:
R$^1$ is hydrogen, alkyl containing 1 to 18 carbon atoms, acyl containing 2 to 18 carbon atoms, carboalkoxy containing 2 to 18 carbon atoms, aminocarbonyl, and acyloxy containing 2 to 18 carbon atoms;
R$^2$ is hydrogen, alkyl containing 1 to 18 carbon atoms, acyl containing 2 to 18 carbon atoms, benzyl or pyridyl; and
R$^3$ is hydrogen, chlorine, bromine or alkyl containing 1 to 18 carbon atoms.

14. A photographic composition as in claim 12 wherein said pyridine compound consists essentially of pyridine.

15. A photographic composition as in claim 12 wherein said pyridine compound consists essentially of 4-picoline.

16. A photographic composition as in claim 12 wherein said photosensitive cyclopropenone consists essentially of a compound represented by the formula:

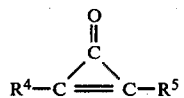

wherein
R$^4$ and R$^5$ are individually alkyl containing 1 to 20 carbon atoms or aryl containing 6 to 20 carbon atoms.

17. A photographic composition as in claim 12 which is a photothermographic composition.

18. A photographic composition as in claim 12 wherein said photosensitive cyclopropenone consists essentially of phenylanisyl cyclopropenone.

19. A photographic composition as in claim 12 wherein said photosensitive cyclopropenone consists of 1-ortho-methoxyphenyl-2-(para-methoxyphenyl)cyclopropenone.

20. A method of producing a dye image in an exposed photographic element as described in claim 1 comprising heating said element to a temperature within the range of 80° C. to 150° C. until a dye image is formed.

21. A method of producing a dye image in an exposed photographic element as described in claim 2 comprising heating said element to a temperature within the range of 80° C. to 150° C. until a dye image is formed.

22. A method of producing a dye image in an exposed photographic element as described in claim 10 comprising heating said element to a temperature within the range of 80° C. to 150° C. until the dye image is formed.

23. A method of producing a dye image in an exposed photographic element as described in claim 11 comprising heating said element to a temperature within the range of 80° C. to 150° C. until the dye image is formed.

24. In an exposed and processed photographic element comprising a dye image, the improvement wherein:
said dye image comprises an oxoindolizine or oxoindolizinium dye.

25. An exposed and processed photographic element as in claim 24 wherein said oxoindolizine or oxoindolizinium dye image comprises a dye selected from the group consisting of methyleneoxoindolizine, (4-oxoarylene)oxoindolizine, bis-oxoindolizine, 1,2-bis(oxoindolizinyl)ethylene, (2- and 4-aminoarylene)oxoindolizine and pyridiniumoxoindolizine dyes.

26. An exposed and processed photographic element as in claim 24 wherein said dye image comprises an oxoindolizine dye represented by the formula:

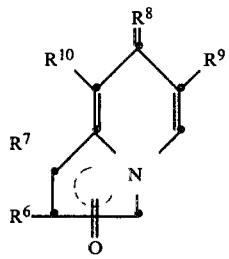

wherein
R$^6$ and R$^7$ are individually selected from alkyl containing 1 to 20 carbon atoms and aryl containing 6 to 20 carbon atoms;
R$^8$ is a divalent group which with the indolizinone nucleus completes an organic chromophore;
R$^9$ is alkyl containing 1 to 18 carbon atoms, acyl containing 2 to 18 carbon atoms, carboalkoxy containing 1 to 18 carbon atoms, aminocarbonyl, acyloxy containing 2 to 18 carbon atoms, bromine or chlorine; and
R$^{10}$ is hydrogen, chlorine, bromine or alkyl containing 1 to 18 carbon atoms.

27. An exposed and processed photographic element as in claim 24 wherein said dye image comprises an oxoindolizinium dye represented by the formula:

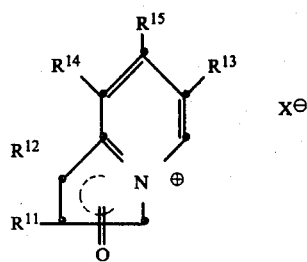

wherein

X is an anion;

$R^{11}$ and $R^{12}$ are individually selected from alkyl containing 1 to 20 carbon atoms and aryl containing 6 to 20 carbon atoms;

$R^{13}$ is hydrogen, alkyl containing 1 to 18 carbon atoms, acyl containing 2 to 18 carbon atoms, carboalkoxy containing 1 to 18 carbon atoms, aminocarbonyl, acyloxy containing 2 to 18 carbon atoms, bromine or chlorine;

$R^{14}$ is hydrogen, chlorine, bromine or alkyl containing 1 to 18 carbon atoms; and $R^{15}$ is a monovalent group which with the indolizinium nucleus completes an organic chromophore.

28. An exposed and processed photographic element as in claim 24 wherein said dye image comprises an oxoindolizine dye represented by the formula:

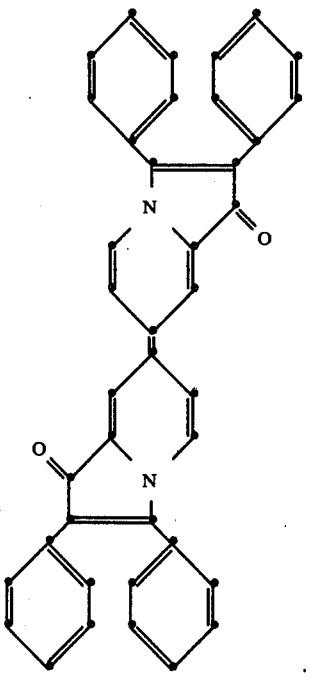

29. A photographic composition comprising 1-phenyl-2-(p-methoxyphenyl)cyclopropenone and 1-methyl-4-(4-pyridyl)pyridinium-p-toluenesulfonate.

30. A photographic composition comprising phenylanisyl cyclopropenone and 4-azastyryl-1-methylpyridinium-p-toluenesulfonate.

* * * * *

UNITED STATES PATENT AND TRADEMARK OFFICE
CERTIFICATE OF CORRECTION

PATENT NO. : 4,368,247   Page 1 of 6

DATED : January 11, 1983

INVENTOR(S) : George L. Fletcher, Jr. et al

It is certified that error appears in the above-identified patent and that said Letters Patent are hereby corrected as shown below:

Column 3, line 31, delete "B";

Column 6, line 8, after "methylaminocarbonyl," insert
-- dimethylaminocarbonyl and ethylaminocarbonyl; --;

Column 6, structure "P-6", "$CH_3-^+N$" should read "$CH_3-\overset{\oplus}{N}$";

Column 11, line 8, "(2,4-dimethylphenyl)-cyclo-" should read "(2,4-dimethylphenyl)cyclo-";

Column 15, line 59, "$R^{36}$" should read "$R^{37}$";

UNITED STATES PATENT AND TRADEMARK OFFICE
CERTIFICATE OF CORRECTION

PATENT NO. : 4,368,247
DATED : January 11, 1983
INVENTOR(S) : George L. Fletcher, Jr. et al It is certified that error appears in the above-identified patent and that said Letters Patent are hereby corrected as shown below:

Column 20, lines 40-45, the structure reading (XII)

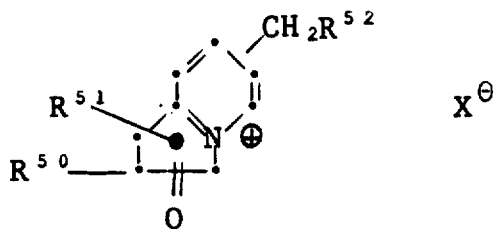

should read (XII)

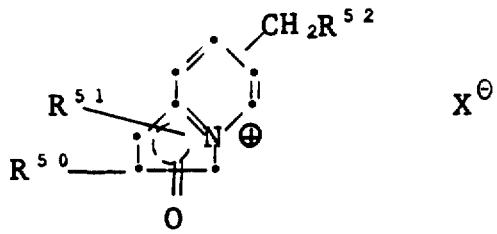

Column 21, line 62, "chlorine fluorine" should read "chlorine, fluorine,";

UNITED STATES PATENT AND TRADEMARK OFFICE
CERTIFICATE OF CORRECTION

PATENT NO. : 4,368,247

DATED : January 11, 1983

INVENTOR(S) : George L. Fletcher, Jr. et al

It is certified that error appears in the above-identified patent and that said Letters Patent are hereby corrected as shown below:

Column 31, lines 55-60, the structure reading (XVI)

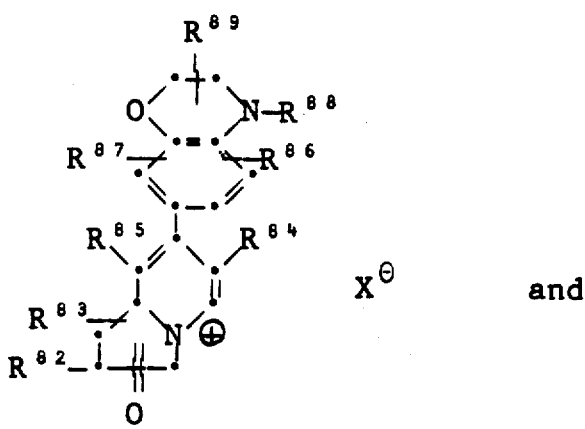

and should read (XVI)

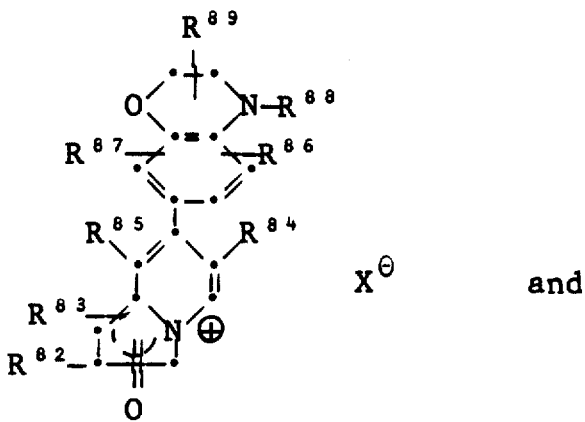

and

UNITED STATES PATENT AND TRADEMARK OFFICE
CERTIFICATE OF CORRECTION

PATENT NO. : 4,368,247
DATED : January 11, 1983
INVENTOR(S) : George L. Fletcher, Jr. et al It is certified that error appears in the above-identified patent and that said Letters Patent are hereby corrected as shown below:

Column 39, lines 40-45, the part of the structure reading "N +" should read "N⊕";

Column 46, line 36, "cyclohexylenedimethyl-ene" should read "cyclohexylenedimethylene";

Column 52, the structure reading

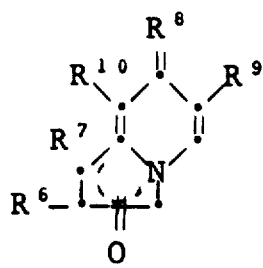

should read

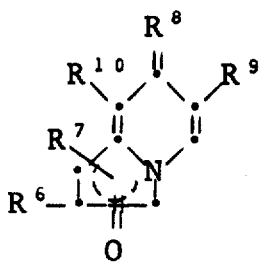

UNITED STATES PATENT AND TRADEMARK OFFICE
CERTIFICATE OF CORRECTION

PATENT NO. : 4,368,247            Page 5 of 6
DATED : January 11, 1983
INVENTOR(S) : George L. Fletcher, Jr. et al It is certified that error appears in the above-identified patent and that said Letters Patent are hereby corrected as shown below:

Column 53, lines 5-10, the structure reading

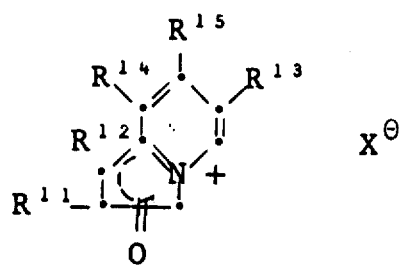

UNITED STATES PATENT AND TRADEMARK OFFICE
CERTIFICATE OF CORRECTION

PATENT NO. : 4,368,247

DATED : January 11, 1983

INVENTOR(S) : George L. Fletcher, Jr. et al.

It is certified that error appears in the above-identified patent and that said Letters Patent is hereby corrected as shown below:

should read

-- 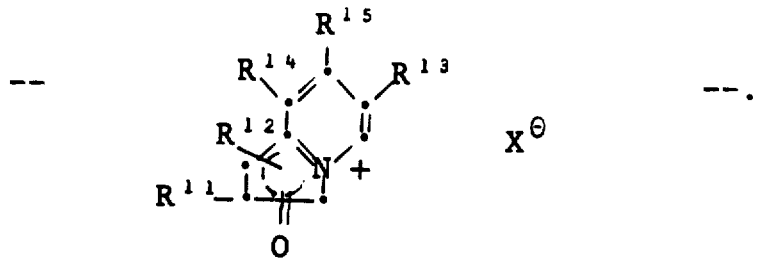 --.

[SEAL]

Signed and Sealed this

Fifth Day of July 1983

Attest:

GERALD J. MOSSINGHOFF

Attesting Officer

Commissioner of Patents and Trademarks